United States Patent
Dubrow et al.

(10) Patent No.: US 7,553,371 B2
(45) Date of Patent: Jun. 30, 2009

(54) POROUS SUBSTRATES, ARTICLES, SYSTEMS AND COMPOSITIONS COMPRISING NANOFIBERS AND METHODS OF THEIR USE AND PRODUCTION

(75) Inventors: Robert Dubrow, San Carlos, CA (US); Carlos Guillermo Casillas, Santa Cruz, CA (US); William P. Freeman, San Mateo, CA (US); Jay L. Goldman, Mountain View, CA (US); Veeral Dilip Hardev, Redwood City, CA (US); Francisco Leon, Palo Alto, CA (US); Chunming Niu, Palo Alto, CA (US); Cheri X. Y. Pereira, Fremont, CA (US)

(73) Assignee: Nanosys, Inc., Palo Alto, CA (US)

( * ) Notice: Subject to any disclaimer, the term of this patent is extended or adjusted under 35 U.S.C. 154(b) by 160 days.

(21) Appl. No.: 11/331,445

(22) Filed: Jan. 11, 2006

(65) Prior Publication Data

US 2009/0143227 A1 Jun. 4, 2009

Related U.S. Application Data

(63) Continuation-in-part of application No. 10/941,746, filed on Sep. 15, 2004.

(60) Provisional application No. 60/541,463, filed on Feb. 2, 2004.

(51) Int. Cl.
*C30B 28/12* (2006.01)
(52) U.S. Cl. .......................... 117/90; 977/742; 977/749; 977/753
(58) Field of Classification Search ................. 977/742, 977/749, 753; 117/90
See application file for complete search history.

(56) References Cited

U.S. PATENT DOCUMENTS

| | | | |
|---|---|---|---|
| 3,651,030 A | 3/1972 | Desaulniers et al. |
| 5,196,396 A | 3/1993 | Lieber et al. |
| 5,226,913 A | 7/1993 | Pinchuk |
| 5,252,835 A | 10/1993 | Lieber et al. |
| 5,274,602 A | 12/1993 | Glen et al. |
| 5,332,910 A | 7/1994 | Haraguchi et al. |

(Continued)

FOREIGN PATENT DOCUMENTS

WO 02080280 10/2002

(Continued)

OTHER PUBLICATIONS

"Stain Resistant Pants are so 'Last Week'; Try the Odor-Free Socks", Small Times, Oct. 3, 2003.*

(Continued)

*Primary Examiner*—Robert M Kunemund
*Assistant Examiner*—G. Nagesh Rao
(74) *Attorney, Agent, or Firm*—Quine Intellectual Property Law Group, P.C.; Monica Elrod-Erickson; Andrew L. Filler

(57) ABSTRACT

Porous and/or curved nanofiber bearing substrate materials are provided having enhanced surface area for a variety of applications including as electrical substrates, semipermeable membranes and barriers, structural lattices for tissue culturing and for composite materials, production of long unbranched nanofibers, and the like.

1 Claim, 20 Drawing Sheets

U.S. PATENT DOCUMENTS

| | | | |
|---|---|---|---|
| 5,338,430 | A | 8/1994 | Parsonage et al. |
| 5,505,928 | A | 4/1996 | Alivisatos et al. |
| 5,512,131 | A | 4/1996 | Kumar et al. |
| 5,640,343 | A | 6/1997 | Gallagher et al. |
| 5,674,592 | A | 10/1997 | Clark et al. |
| 5,690,807 | A | 11/1997 | Clark, Jr. et al. |
| 5,751,018 | A | 5/1998 | Alivisatos et al. |
| 5,800,706 | A | 9/1998 | Fischer |
| 5,840,435 | A | 11/1998 | Lieber et al. |
| 5,858,862 | A | 1/1999 | Westwater et al. |
| 5,897,945 | A | 4/1999 | Lieber et al. |
| 5,953,595 | A | 9/1999 | Gosain et al. |
| 5,962,863 | A | 10/1999 | Russell et al. |
| 5,976,957 | A | 11/1999 | Westwater et al. |
| 5,990,479 | A | 11/1999 | Weiss et al. |
| 5,997,832 | A | 12/1999 | Lieber et al. |
| 6,004,444 | A | 12/1999 | Aksay et al. |
| 6,036,774 | A | 3/2000 | Lieber et al. |
| 6,048,616 | A | 4/2000 | Gallagher et al. |
| 6,128,214 | A | 10/2000 | Kuekes et al. |
| 6,136,156 | A | 10/2000 | El-Shall et al. |
| 6,159,742 | A | 12/2000 | Lieber et al. |
| 6,190,634 | B1 | 2/2001 | Lieber et al. |
| 6,207,229 | B1 | 3/2001 | Bawendi et al. |
| 6,225,198 | B1 | 5/2001 | Alivisatos et al. |
| 6,235,675 | B1 | 5/2001 | McIlroy |
| 6,248,674 | B1 | 6/2001 | Kamins et al. |
| 6,256,767 | B1 | 7/2001 | Kuekes et al. |
| 6,274,007 | B1 | 8/2001 | Smirnov et al. |
| 6,306,736 | B1 | 10/2001 | Alivisatos et al. |
| 6,321,915 | B1 | 11/2001 | Wilson et al. |
| 6,322,901 | B1 | 11/2001 | Bawendi et al. |
| 6,360,736 | B1 | 3/2002 | Juan |
| 6,380,103 | B2 | 4/2002 | Gonzalez et al. |
| 6,383,923 | B1 | 5/2002 | Brown et al. |
| 6,413,489 | B1 | 7/2002 | Ying et al. |
| 6,438,025 | B1 | 8/2002 | Skarupo |
| 6,447,663 | B1 | 9/2002 | Lee et al. |
| 6,471,761 | B2 | 10/2002 | Fan et al. |
| 6,495,258 | B1 | 12/2002 | Chen et al. |
| 6,566,704 | B2 | 5/2003 | Choi et al. |
| 6,586,785 | B2 | 7/2003 | Flagan et al. |
| 6,760,245 | B2 | 7/2004 | Eaton et al. |
| 6,773,616 | B1 | 8/2004 | Chen et al. |
| 6,781,166 | B2 | 8/2004 | Lieber et al. |
| 6,798,000 | B2 | 9/2004 | Luyken et al. |
| 6,815,218 | B1 | 11/2004 | Jacobson et al. |
| 6,815,750 | B1 | 11/2004 | Kamins |
| 6,831,017 | B1 | 12/2004 | Li et al. |
| 6,858,455 | B2 | 2/2005 | Guillom et al. |
| 6,872,645 | B2 | 3/2005 | Duan et al. |
| 6,878,871 | B2 | 4/2005 | Scher et al. |
| 6,882,051 | B2 | 4/2005 | Majumdar et al. |
| 6,962,823 | B2 | 11/2005 | Empedocles et al. |
| 7,051,945 | B2 | 5/2006 | Stumbo et al. |
| 7,056,409 | B2 | 6/2006 | Dubrow |
| 7,057,881 | B2 | 6/2006 | Chow et al. |
| 7,067,328 | B2 | 6/2006 | Dubrow et al. |
| 7,285,422 | B1 | 10/2007 | Little et al. |
| 2001/0023986 | A1 | 9/2001 | Mancevski |
| 2001/0051367 | A1 | 12/2001 | Kiang |
| 2002/0014667 | A1 | 2/2002 | Shin et al. |
| 2002/0090542 | A1 | 7/2002 | Mosdale et al. |
| 2002/0117659 | A1 | 8/2002 | Lieber et al. |
| 2002/0125192 | A1 | 9/2002 | Lopez et al. |
| 2002/0127495 | A1 | 9/2002 | Scherer |
| 2002/0130311 | A1 | 9/2002 | Lieber et al. |
| 2002/0130353 | A1 | 9/2002 | Lieber et al. |
| 2002/0158342 | A1 | 10/2002 | Tuominen et al. |
| 2002/0163079 | A1 | 11/2002 | Awano |
| 2002/0175408 | A1 | 11/2002 | Majumdar et al. |
| 2002/0179434 | A1 | 12/2002 | Dai et al. |
| 2003/0012723 | A1 | 1/2003 | Clarke |
| 2003/0037675 | A1 | 2/2003 | Gillingham et al. |
| 2003/0042562 | A1 | 3/2003 | Giebeler et al. |
| 2003/0044777 | A1 | 3/2003 | Beattie |
| 2003/0071246 | A1 | 4/2003 | Grigorov |
| 2003/0089899 | A1 | 5/2003 | Lieber et al. |
| 2003/0184357 | A1 | 10/2003 | Dijon et al. |
| 2003/0185741 | A1* | 10/2003 | Matyjaszewski et al. 423/445 R |
| 2003/0186522 | A1 | 10/2003 | Duan et al. |
| 2003/0189202 | A1 | 10/2003 | Li et al. |
| 2003/0200521 | A1 | 10/2003 | DeHon et al. |
| 2003/0222019 | A1 | 12/2003 | Fulton et al. |
| 2004/0005258 | A1 | 1/2004 | Fonash et al. |
| 2004/0012118 | A1* | 1/2004 | Perez et al. .................. 264/257 |
| 2004/0026684 | A1 | 2/2004 | Empedocles |
| 2004/0031975 | A1 | 2/2004 | Kern et al. |
| 2004/0036126 | A1 | 2/2004 | Chau et al. |
| 2004/0036128 | A1 | 2/2004 | Zhang et al. |
| 2004/0061422 | A1 | 4/2004 | Avouris et al. |
| 2004/0095658 | A1 | 5/2004 | Buretea et al. |
| 2004/0112964 | A1 | 6/2004 | Empedocles et al. |
| 2004/0118448 | A1 | 6/2004 | Scher et al. |
| 2004/0121681 | A1* | 6/2004 | Lindsay et al. .............. 442/121 |
| 2004/0135951 | A1 | 7/2004 | Stumbo et al. |
| 2004/0146560 | A1 | 7/2004 | Whiteford et al. |
| 2004/0206448 | A1 | 10/2004 | Dubrow |
| 2005/0026526 | A1 | 2/2005 | Verdegan et al. |
| 2005/0038498 | A1 | 2/2005 | Dubrow et al. |
| 2005/0064618 | A1 | 3/2005 | Brown et al. |
| 2005/0066883 | A1 | 3/2005 | Dubrow et al. |
| 2005/0079659 | A1 | 4/2005 | Duan et al. |
| 2005/0181195 | A1 | 8/2005 | Dubrow |
| 2005/0187605 | A1* | 8/2005 | Greenhalgh et al. ........ 623/1.15 |
| 2005/0279274 | A1 | 12/2005 | Niu et al. |
| 2006/0159916 | A1 | 7/2006 | Dubrow et al. |
| 2006/0188774 | A1 | 8/2006 | Niu et al. |
| 2007/0084797 | A1 | 4/2007 | Cooper et al. |

FOREIGN PATENT DOCUMENTS

| | | |
|---|---|---|
| WO | 03085701 | 10/2003 |
| WO | WO-2005023923 | 3/2005 |

OTHER PUBLICATIONS

Bachtold, A. et al., "Logic Circuits with Carbon Nanotube Transistors" *Science* (2001) 294:1317-1320.

Bjork, M.T. et al. "One-dimensional steeplechase for electrons realized" *Nano Letters* (2002) 2:86-90.

Cao, Y. et al. "Growth and properties of semiconductor core/shell nanocrystals with InAs cores" *J. Am. Chem. Soc.* (2000) 122:9692-9702.

Chen, J. et al., "Observation of a Large On-Off Ratio and Negative Differenital Resistance in an Electronic Molecular Switch" *Science* (1999) 286:1550-1552.

Chung, S-W. et al., "Silicon Nanowire Devices" *App. Phys. Letts.* (2000) 76(15):2068-2070.

Collier, C.P. et al., "Electronically Configurable Molecular-Based Logic Gates" *Science* (1999) 285:391-394.

Cui, Y. et al. "Doping and electrical transport in silicon nanowires" *J. Phys. Chem. B* (2000) 104:5213-5216.

Cui, Y. et al. "Diameter-controlled synthesis of single-crystal silicon nanowires" *Appl. Phys. Lett.* (2001) 78:2214-2216.

Cui, Y. et al., "Functional Nanoscale electronic devices assembled using silicon nanowire building blocks" *Science* (2001) 291:851-853.

Dabbousi, B.O. et al. "(CdSe)ZnS core-shell quantum dots: Synthesis and characterization of a size series of highly luminescent nanocrystallites" *J. Phys. Chem. B* (1997) 101:9463-9475.

Derycke, V. et al., "Carbon Nanocule Inter-and Intramolecular Logic Gates" *Nano Letters* (2001) 1(9):453-456.

Duan, X. et al., "General synthesis of compound semiconductor nanowires" *Adv. Mater.* (2000) 12:298-302.

Duan, X. et al., "High performance thin-film transistors using semiconductor nanowires and nanoribbons" *Nature* (2003) 425:274-278.

Givargizov, E.I. "Fundamental Aspects of VLS Growth" *J. Cryst. Growth* (1975) 31:20-30.

Greene, L. et al. "Low-temperature wafer scale production of ZnO nanowire arrays", *Angew. Chem. Int. Ed.* (2003) 42:3031-3034.

Gudiksen, M.S. et al "Diameter-selective synthesis of semiconductor nanowires" *J. Am. Chem. Soc.* (2000) 122:8801-8802.

Gudiksen, M.S. et al. "Synthetic control of the diameter and length of single crystal semiconductor nanowires" *J. Phys. Chem. B* (2001) 105:4062-4064.

Gudiksen, M.S. et al. "Growth of nanowire superlattice structures for nanoscale photonics and electronics" *Nature* (2002) 415:617-620.

Haraguchi, K. et al., "Polarization Dependence of Ligh Emitted from GaAs p-n junctions in quantum wire crystals" *J. Appl. Phys.* (1994) 75(8):4220-4225.

Haraguchi, K. et al., "Self Organized Fabrication of Planar GaAs Nanowhisker Arrays" *Appl. Phys. Lett.* (1996) 69(3):386-387.

Hiruma, K. et al., "GaAs Free Standing Quantum Sized Wires" *J. Appl. Phys.* (1993) 74(5):3162-3171.

Huang, Y. et al., "Directed Assembly of One-Dimensional Nanostructures into Functional networks" *Science* (2001) 291:630-633.

Huang, Y. et al., "Logic Gates and Computation from Assembled Nanowire Building Blocks" *Science* (2001) 294:1313-1317.

Jun, Y-W. et al. "Controlled synthesis of multi-armed CdS nanorod architectures using monosurfactant system" *J. Am. Chem. Soc.* (2001) 123:5150-5151.

Kong, J. et al., "Synthesis of individual single-walled carbon nanotubes on patterned silicon wafers" *Nature* (1998) 395:878-881.

Kong, J. et al., "Chemical vapor deposition of methane for single-walled carbon nanotubes" *Chem. Phys. Lett.*(1998) 292:567-574.

Kong, J. et al., "Nanotube molecular wires as chemical sensors" *Science* (2000) 287:622-625.

Liu, C. et al. "Sol-Gel Synthesis of Free-Standing Ferroelectric Lead Zirconate Titanate Nanoparticles" *J. Am. Chem. Soc.* (2001) 123:4344-4345.

Manalis, S.F. et al., "Microvolume field-effect pH sensor for the scanning probe microscope" *Applied Phys. Lett.* (2000) 76:1072-1074.

Manna, L. et al. "Synthesis of Soluble and Processable Rod-,Arrow-, Teardrop-, and Tetrapod-Shaped CdSe Nanocrystals" *J. Am. Chem. Soc.* (2000) 122:12700-12706.

Manna, L. et al. "Epitaxial growth and photochemical annealing of graded CdS/ZnS shells on colloidal CdSe nanorods" *J. Am. Chem. Soc.* (2002) 124:7136-7145.

Martin, C.R., "Nanomaterials: A membrane-based synthetic approach" Science 266:1961-1966.

Morales, A.M. et al. "A laser ablation method for the synthesis of crystalline semiconductor nanowires" *Science* (1998) 279:208-211.

Peng, X et al. "Epitaxial growth of highly luminescent CdSe/CdS core/shell nanocrystals with photostability and electronic accessibility" *J. Am. Chem. Soc.* (1997) 119:7019-7029.

Peng, X. et al. "Shape Control of CdSe Nanocrystals" *Nature* (2000) 404:59-61.

Rabin, O. et al. "Formation of thick porous anodic alumina films and nanowire arrays on silicon wafers and glass" *Adv. Func. Mater.* (2003) 13(8):631-638.

Puntes, V.F. et al. "Colloidal nanocrystal shape and size control: The case of cobalt" *Science* (2001) 291:2115-2117.

Schon J.H. et al., "Field-effect modulation of the conductance of single molecules" *Science* (2001) 294:2138-2140.

Schon, J.H. et al., "Self-assembled monolayer organic field-effect transistors" (2001) *Nature* 413:713-716.

Service, R.F., "Assembling nanocircuits from the bottom up" *Science* (2001) 293:782-785.

Tang, T. et al., "Synthesis of InN Nanowires Using a Two-Zone Chemical Vapor Deposition Approach" IEEE (Aug. 14, 2003) 205-207.

Tans, S.J. et al., "Room-temperature transistor based on a single carbon nanotube" *Nature* (1998) 393:49-52.

Thess, A. et al., "Crystalline ropes of metallic carbon nanotubes" (1996) *Science* 273:483-486.

Tseng, G.Y. et al., "Toward nanocomputers" (2001) *Science* 294:1293-1294.

Urban, J.J. et al. "Synthesis of single-crystalline perovskite nanowires composed of barium titanate and strontium titanate" *J. Am. Chem. Soc.* (2002) 124(7):1186-1187.

Wagner, R.S. et al., "Vapor-Liquid-Solid mechanism of single crystal growth" *Appl. Phys. Lett.* (1964) 4(5):89-90.

Wang, D. et al., "Low Temperature Synthesis of Single-Crystal Germanium Nanowires by Chemical Vapor Deposition" *Angew. Chem. Int. Ed.* (2002) 41(24):4783-4786.

Wu, Y et al. "Block-by-block growth of single-crystalline Si/SiGe superlattice nanowires" *Nano Letters* (2002) 2(2):83-86.

Yamada, T. "Analysis of submicron carbon nanotube field-effect transistors" *Appl. Phys. Letts* (2000) 76(5):628-630.

Yazawa, M. et al. "Semiconductor nanowhiskers" *Adv. Mater.(1993)* 5(7/8):577-580.

Yun, W.S. et al. "Ferroelectric Properties of Individual Barium Titanate Nanowires Investigated by Scanned Probe Microscopy" *Nanoletters* (2002) 2(5):447-450.

Zhou, C. et al., "Nanoscale metal/self-assembled monolayer/metal heterostructures" *Applied Phys. Lett* (1997) 71:611-613.

* cited by examiner

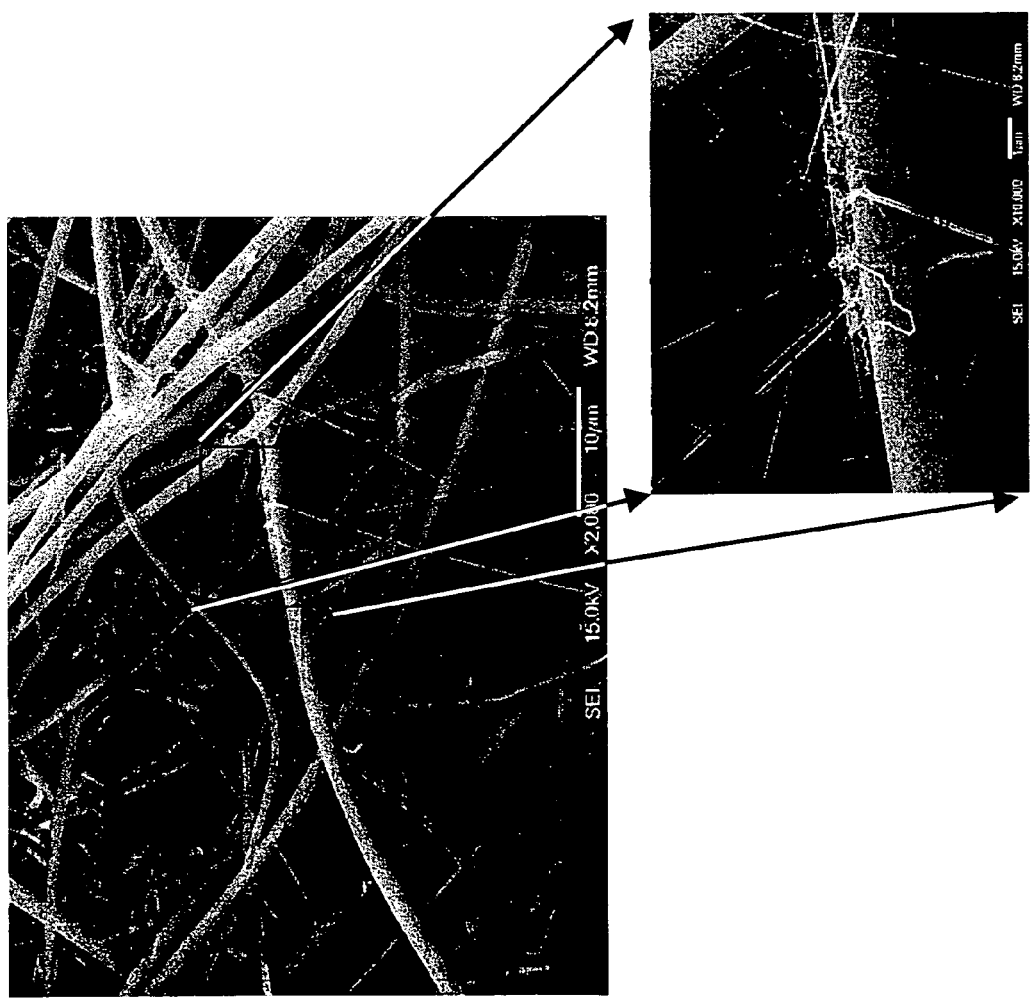

POROUS SUBSTRATES, ARTICLES, SYSTEMS AND COMPOSITIONS COMPRISING NANOFIBERS AND METHODS OF THEIR USE AND PRODUCTION

CROSS REFERENCE TO RELATED APPLICATIONS

This application is a continuation-in-part of U.S. patent application Ser. No. 10/941,746, filed Sep. 15, 2004, entitled "POROUS SUBSTRATES, ARTICLES, SYSTEMS AND COMPOSITIONS COMPRISING NANOFIBERS AND METHODS OF THEIR USE AND PRODUCTION" by Dubrow and Niu, which claims priority to and benefit of provisional U.S. Patent Application Ser. No. 60/541,463, filed Feb. 2, 2004, the full disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

Portions of this invention may have been made with United States Government support under Contract No. W91QY-05-C-0081 from U.S. Army Soldier Systems Center (SSC), Natick, Mass. As such, the United States Government may have certain rights in the invention.

FIELD OF THE INVENTION

The invention relates primarily to the field of nanotechnology. More specifically, the invention pertains to nanofibers, including methods of synthesizing or stabilizing nanofibers, articles comprising nanofibers, and use of nanofibers in various applications.

BACKGROUND OF THE INVENTION

Nanotechnology has been simultaneously heralded as the next technological evolution that will pave the way for the next societal evolution, and lambasted as merely the latest batch of snake oil peddled by the technically overzealous. Fundamentally, both sides of the argument have a number of valid points to support their position. For example, it is absolutely clear that nanomaterials possess very unique and highly desirable properties in terms of their chemical, structural and electrical capabilities. However, it is also clear that, to date, there is very little technology available for integrating nanoscale materials into the macroscale world in a reasonable commercial fashion and/or for assembling these nanomaterials into more complex systems for the more complex prospective applications, e.g., nanocomputers, nanoscale machines, etc. A variety of researchers have proposed a number of different ways to address the integration and assembly questions by waving their hands and speaking of molecular self assembly, electromagnetic assembly techniques and the like. However, there has been either little published success or little published effort in these areas.

In certain cases, uses of nanomaterials have been proposed that exploit the unique and interesting properties of these materials more as a bulk material than as individual elements requiring individual assembly. For example, Duan et al., Nature 425:274-278 (September 2003), describes a nanowire based transistor for use in large area electronic substrates, e.g., for displays, antennas, etc., that employs a bulk processed, oriented semiconductor nanowire film or layer in place of a rigid semiconductor wafer. The result is an electronic substrate that performs on par with a single crystal wafer substrate, but that is manufacturable using conventional and less expensive processes that are used in the poorer performing amorphous semiconductor processes. In accordance with this technology, the only new process requirement is the ability to provide a film of nanowires that are substantially oriented along a given axis. The technology for such orientation has already been described in detail in, e.g., International Patent Application Nos. PCT/US03/09827, PCT/US03/09991, both filed Apr. 1, 2003, and PCT/US03/30637, filed Sep. 30, 2003, as well as U.S. patent application Ser. No. 10/673,092, filed Sep. 25, 2003, (the full disclosures of each of which are hereby incorporated by reference herein, in their entirety for all purposes) and is readily scalable to manufacturing processes.

In another exemplary case, bulk processed nanocrystals have been described for use as a flexible and efficient active layer for photoelectric devices. In particular, the ability to provide a quantum confined semiconductor crystal in a hole conducting matrix (to provide type-II bandgap offset), allows the production of a photoactive layer that can be exploited either as a photovoltaic device or photoelectric detector. When disposed in an active composite, these nanomaterials are simply processed using standard film coating processes that are available in the industry. See, e.g., U.S. patent application Ser. No. 10/656,802, filed Sep. 4, 2003, and incorporated herein by reference in its entirety for all purposes.

In accordance with the expectation that the near term value of nanotechnology requires the use of these materials in more of a bulk or bulk-like process, certain aspects of the present invention use nanomaterials not as nanomaterials per se, but as a modification to larger materials, compositions and articles to yield fundamentally novel and valuable materials compositions and articles.

BRIEF SUMMARY OF THE INVENTION

The present invention is directed, in one aspect, to a novel presentation of nanomaterials that enables a broader use and application of those materials while imparting ease of handling, fabrication, and integration that is lacking in previously reported nanomaterials. In particular, one aspect of the present invention provides a porous substrate upon which is attached a plurality of nanofibers. The nanofibers may be attached to any portion or over the entire overall surface of the substrate or may be localized primarily or substantially upon the interior wall surfaces of the apertures that define the pores that are disposed through the porous substrate.

The articles of the invention may be employed as filtration media to filter gas, fluids or the like, or they may be employed as semipermeable barriers, e.g., breathable moisture barriers for outerwear, bandages, or the like. The articles of the invention may also be employed to integrate nanomaterials into electronic devices, in which the nanomaterials impart useful characteristics, e.g., as electrodes and or other active elements in photovoltaic devices and the like, or they may be used to integrate these nanomaterials into physical structures, e.g., composites, or biological structures, e.g., tissue. Synthesis of nanofibers on a porous or curved substrate can facilitate production of large numbers and/or a high density of long, unbranched nanofibers for use in any of a variety of applications.

Thus, a first general class of embodiments provides methods of producing nanofibers. In the methods, a substrate comprising a) a plurality of apertures disposed therethrough, the substrate comprising an overall surface area that includes an interior wall surface area of the plurality of apertures, or b) a curved surface is provided. A plurality of nanofibers is synthesized on the substrate, wherein the resulting nanofibers are attached to at least a portion of the overall surface area of the substrate of a) or to at least a portion of the curved surface of b).

The substrate can comprise a solid substrate with a plurality of pores disposed through it, a mesh (e.g., a metallic mesh, e.g., a mesh comprising a metal selected from the group consisting of: nickel, titanium, platinum, aluminum, gold, and iron), a woven fabric (e.g., an activated carbon fabric), or a fibrous mat (e.g., comprising glass, quartz, silicon, metallic, or polymer fibers). As other examples, the substrate can comprise a plurality of microspheres (e.g., glass or quartz microspheres), a plurality of fibers, e.g., glass or quartz fibers (e.g., microfibers, fiberglass, glass or quartz fiber filters), or a foam. In certain embodiments, the plurality of apertures in the substrate of a) have an effective pore size of less than 10 $\mu$m, less than 1 $\mu$m, less than 0.5 $\mu$m, or even less than 0.2 $\mu$m. In other embodiments, the plurality of apertures in the substrate of a) have an effective pore size of at least 25 $\mu$m, at least 50 $\mu$m, at least 100 $\mu$m, or more.

The nanofibers can comprise essentially any type of nanofibers. In certain embodiments, the nanofibers comprise nanowires, and the methods can include synthesizing the plurality of nanowires by depositing a gold colloid on at least a portion of the overall surface area of the substrate of a) or on at least a portion of the curved surface of b) and growing the nanowires from the gold colloid, e.g., with a VLS synthesis technique. The plurality of nanofibers optionally comprises a semiconductor material selected from group IV, group II-VI and group III-V semiconductors (e.g., silicon).

The methods optionally include surrounding or at least partially encapsulating the substrate and the resulting attached nanofibers with a matrix material; dissolving a soluble substrate following synthesis of the nanofibers on the substrate; forming a coating on the resulting nanofibers, wherein the coating is contiguous between adjacent nanofibers; disposing a layer of porous material on the resulting nanofibers (and optionally disposing the substrate on a second layer of porous material, sandwiching the nanofiber-bearing substrate); and/or functionalizing the nanofibers (e.g., by attaching a chemical moiety or nanocrystal to their surface).

In one class of embodiments, yield of the resulting nanofibers having a length greater than 10 $\mu$m (e.g., greater than 20 $\mu$m, 30 $\mu$m, 40 $\mu$m, 50 $\mu$m, or 60 $\mu$m) is at least 10% greater than yield of nanofibers of that length synthesized on a planar non-porous substrate of the same surface area using substantially the same growth process. The yield from the methods is optionally at least 25%, 50%, 75%, or even 100% greater than the yield from growth on the planar non-porous substrate.

The nanofibers are optionally removed from the surface area of the substrate of a) or the curved surface of b) following synthesis of the nanofibers, e.g., by sonicating the substrate, to produce a population of detached nanofibers. In one class of embodiments, at least 10% of the nanofibers in the population of detached nanofibers have a length greater than 10 $\mu$m, 20 $\mu$m, 30 $\mu$m, 40 $\mu$m, 50 $\mu$m, or 60 $\mu$m, while at most 50% of the nanofibers have a length less than 10 $\mu$m.

Articles or populations of nanofibers produced by the methods form another feature of the invention. Thus, one exemplary class of embodiments provides an article comprising a substrate having a curved surface, and a plurality of nanofibers (e.g., nanowires) attached to at least a portion of the curved surface of the substrate. The substrate can comprise, e.g., a plurality of microspheres or one or more glass fiber, quartz fiber, metallic fiber, polymer fiber, or other fiber.

As for the embodiments above, the plurality of nanofibers optionally comprises a semiconductor material selected from group IV, group II-VI and group III-V semiconductors (e.g., silicon). Optionally, at least 10% of the nanofibers present on the curved surface have a length greater than 10 $\mu$m, 20 $\mu$m, 30 $\mu$m, 40 $\mu$m, 50 $\mu$m, or 60 $\mu$m, while at most 50% of the nanofibers present on the curved surface have a length less than 10 $\mu$m. The nanofibers can be preformed and deposited on the substrate to produce the article, or the plurality of nanofibers can be attached to the portion of the curved surface by having been grown on the portion of the curved surface. The article optionally includes a matrix material surrounding at least a portion of the curved surface and plurality of nanofibers. Devices or compositions including the article form another feature of the invention, for example, an implantable medical device comprising an article of the invention, e.g., attached to and covering at least a portion of the surface of the implantable medical device.

Another general class of embodiments provides methods of stabilizing nanofibers (e.g., nanowires). In the methods, a population of nanofibers is provided, and a coating is formed on the nanofibers. The coating is contiguous between adjacent nanofibers in the population. A first material comprising the nanofibers is optionally different from a second material comprising the coating. In one class of embodiments, the coating comprises a carbide, a nitride, or an oxide, e.g., an oxide of silicon, titanium, aluminum, magnesium, iron, tungsten, tantalum, iridium, or ruthenium, or an oxide of the material comprising the nanofibers. In another class of embodiments, the nanofibers are comprised of silicon and the coating is comprised of polysilicon.

The population of nanofibers is optionally provided by synthesizing the nanofibers on a surface of a substrate. The methods can include functionalizing the coating with a chemical binding moiety, a hydrophobic chemical moiety, a hydrophilic chemical moiety, or the like.

Populations of nanofibers formed by the methods are another feature of the invention. One general class of embodiments provides a population of nanofibers that includes nanofibers (e.g., nanowires) and a coating on the nanofibers, wherein the coating is contiguous between adjacent nanofibers in the population. As for the methods described above, a first material comprising the nanofibers is optionally different from a second material comprising the coating. In one class of embodiments, the coating comprises a carbide, a nitride, or an oxide, e.g., an oxide of silicon, titanium, aluminum, magnesium, iron, tungsten, tantalum, iridium, or ruthenium, or an oxide of the material comprising the nanofibers. In another class of embodiments, the nanofibers are comprised of silicon and the coating is comprised of polysilicon. The coating can be functionalized with a chemical binding moiety, a hydrophobic chemical moiety, a hydrophilic chemical moiety, or the like. The nanofibers are optionally attached to a substrate. In one embodiment, the nanofibers are attached to and cover at least a portion of a surface of an implantable medical device.

Yet another general class of embodiments provides an article comprising a substrate having a plurality of apertures disposed therethrough, the substrate comprising an overall surface area that includes an interior wall surface area of the plurality of apertures, and a plurality of nanofibers attached to at least a portion of the overall surface area of the substrate. The substrate can comprise, for example, a solid substrate (e.g., a silica based wafer, a metallic plate, or a ceramic sheet or plate) while the plurality of apertures comprises a plurality of pores disposed through the solid substrate. As another example, the substrate can comprise a mesh, e.g., a polymer mesh or a metallic mesh (comprising, e.g., nickel, titanium, platinum, aluminum, gold, or iron). As yet another example, the substrate can comprise a woven fabric, e.g., a fabric comprising fiberglass, carbon fiber, or a polymer (e.g., polyimide, polyetherketone, or polyaramid). As yet another example, the substrate can comprise a fibrous mat, e.g., a fibrous mat comprising silica based fibers (e.g., glass and silicon), metallic fibers, or polymer fibers.

In certain embodiments, the plurality of apertures have an effective pore size of less than 10 µm, for example, less than 1 µm, less than 0.5 µm, or less than 0.2 µm. In other embodiments, for example, embodiments in which synthesis of long unbranched nanofibers are desired, the plurality of apertures have an effective pore size of at least 25 µm, at least 50 µm, at least 100 µm, or more.

The nanofibers (e.g., nanowires) can comprise essentially any suitable material. For example, the plurality of nanofibers can comprise a semiconductor material selected from group IV, group II-VI and group III-V semiconductors, e.g., silicon. The nanofibers can be pre-formed and deposited on the substrate, or they can be attached to the portion of the overall surface area of the substrate by having been grown on the portion of the surface area. The plurality of nanofibers is optionally electrically coupled to the substrate. The plurality of nanofibers can be functionalized with a chemical binding moiety, e.g., a hydrophobic chemical moiety.

In one class of embodiments, a matrix material surrounds or at least partially encapsulates the substrate and plurality of nanofibers. The matrix material can at least partially intercalate into the apertures. In one embodiment, the matrix material and the plurality of nanofibers have a type-II energy band-gap offset with respect to each other. The matrix material optionally comprises a polymer, for example, a polyester, an epoxy, a urethane resin, an acrylate resin, polyethylene, polypropylene, nylon, or PFA. In one aspect, the invention provides implantable medical devices. For example, an implantable medical device can include an article of the invention attached to and covering at least a portion of a surface of the implantable medical device.

In one class of embodiments, the substrate comprises activated carbon, e.g., an activated carbon fabric. At least a first population of nanocrystals can be attached to the nanofibers, for example, nanocrystals comprising a material selected from the group consisting of: Ag, ZnO, CuO, $Cu_2O$, $Al_2O_3$, $TiO_2$, MgO, FeO, and $MnO_2$. At least a second population of nanocrystals is optionally also attached to the nanofibers, where the nanocrystals of the second population comprise a different material than do the nanocrystals of the first population. In certain embodiments, the nanofibers are functionalized with a chemical moiety, e.g., a chemical moiety that absorbs or decomposes a non-organic gas. Preferred nanofibers in these embodiments include carbon nanotubes and silicon nanowires. An article of clothing can comprise the nanofiber-enhanced substrate of the invention.

Various techniques can be used to protect the nanofiber bearing substrate. For example, in one class of embodiments, the substrate (e.g., a woven fabric) comprises a first surface, and the article further comprises a first layer of porous material disposed on the first surface of the substrate. Optionally, the substrate comprises a second surface, and the article also includes a second layer of porous material disposed on the second surface of the substrate, whereby the substrate is sandwiched between the first and second layers of porous material. As another example, the article can include a coating on the nanofibers, which coating is contiguous between adjacent nanofibers.

Yet another general class of embodiments provides methods of producing a vapor absorbing fabric. In the methods, a porous fabric substrate that comprises a plurality of apertures disposed therethrough is provided. The substrate comprises an overall surface area that includes an interior wall surface area of the plurality of apertures. A plurality of nanofibers attached to at least a portion of the overall surface area of the fabric substrate is also provided, and the nanofibers are functionalized with a moiety that absorbs or decomposes at least one organic or non-organic gas, thereby producing a vapor absorbing fabric.

The fabric is preferably an activated carbon fabric. The nanofibers can be functionalized with a chemical moiety that absorbs or decomposes at least one non-organic gas. Preferably, the nanofibers are functionalized by attaching at least a first population of nanocrystals to the nanofibers, which first population of nanocrystals comprises a first material that absorbs or decomposes at least one non-organic gas. The vapor absorbing fabric can be incorporated into an article of clothing or other protective apparatus.

A related class of embodiments also provides methods of producing a vapor absorbing fabric. In the methods, a porous fabric substrate that comprises a plurality of apertures disposed therethrough is provided (e.g., a mesoporous carbon fabric). The substrate comprises an overall surface area that includes an interior wall surface area of the plurality of apertures. A plurality of nanocrystals is attached to at least a portion of the overall surface area of the fabric substrate, which nanocrystals absorb or decompose at least one non-organic gas, thereby producing the vapor absorbing fabric.

DETAILED DESCRIPTION

I. General Description of the Invention

Figure 1A:
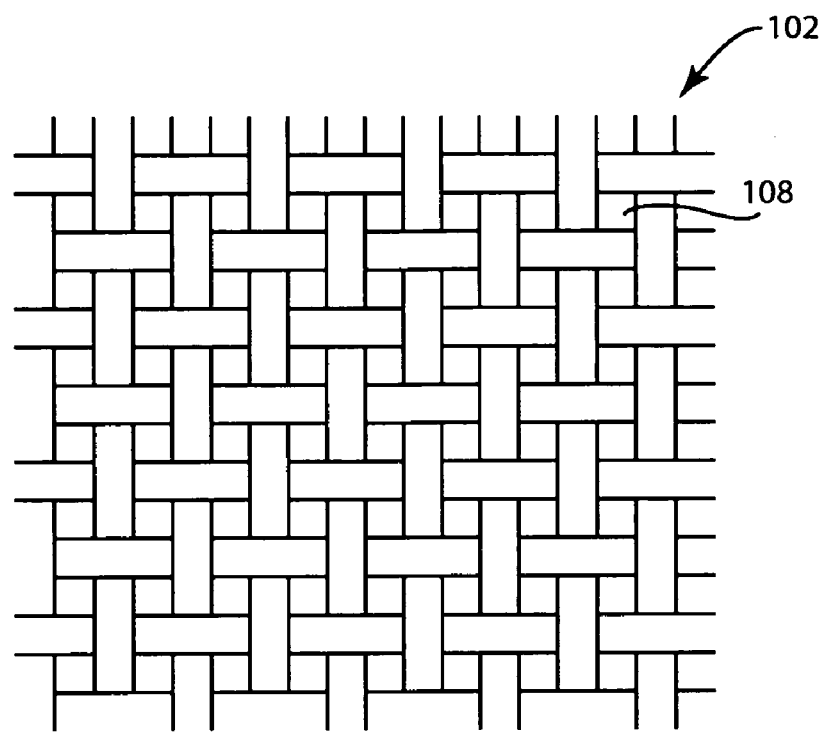
FIG. 1 Panels A and B show a schematic illustration of a porous substrate having nanowires attached to its surfaces.

The present invention generally provides, inter alia, novel articles and compositions that employ nanowire surfaces or surface portions to impart unique physical, chemical and electrical properties. In particular, the present invention is directed, in part, to porous substrates that have nanowires attached to at least a portion of the overall surfaces of the porous substrates in order to provide materials that have a wide range of unique and valuable properties for a wide range of different applications.

The application of nanowires to the various surfaces of porous substrates not only improves the performance of porous substrates in applications where they are already used, but also improves performance of substrate materials in a number of other different applications, where such porous substrates may or may not conventionally be employed.

By way of example, incorporation of nanowire enhanced surfaces in membranes or other semi-permeable barriers can enhance filtration efficiencies. In particular, by providing nanowires within the pores of existing membranes or other permeated layers, one can provide higher filtration efficiencies without the expected increase in pressure drop across the filter (see Grafe et al., Nanowovens in Filtration-Fifth International Conference, Stuttgart, Germany, March 2003). Relatedly, such nanofibers may be used to impart alternate properties to such barriers, e.g., breathable moisture repellant barriers, antibacterial/antiseptic barriers. Such barriers would be widely applicable in the outdoor clothing industry but would also be particularly useful as bandages or surgical dressings due to their permeability to oxygen but impermeability to moisture or particles including bacteria, as well as the use of antimicrobial nanofibers. This latter application is particularly interesting in light of the dry adhesive characteristics of nanowire/nanofiber enhanced surfaces (see, e.g., U.S. patent application Ser. No. 10/661,381, filed Sep. 12, 2003, incorporated herein by reference in its entirety for all purposes). Relatedly, such nanofiber enhanced surfaces can also be used in the construction of chemical and/or biological protective barriers, e.g., clothing, optionally permeable to moisture but absorbing chemical vapors.

While some researchers have proposed depositing nanofibers onto membranes to achieve higher surface areas, the ability to attach fibers to the surface, and particularly to grow such fibers in situ, provides numerous advantages over simple deposition of fibers. In particular, in merely depositing fibers on membranes, it is difficult to get uniform or complete, e.g., penetrating, coverage of the fibers over the total surface area of the membrane, whereas in situ growth methods give far better coverage of interior surfaces, and thus provide much greater surface area for the membrane or barrier. Additionally, such methods provide for varied orientations of such fibers from the surfaces to which they are attached, i.e., having fibers extend from the surface as opposed to laying flat against the surface.

In addition to improving the function of porous substrates, the use of porous substrates in conjunction with nanofibers/nanowires also provides a unique, ultra high surface area material that can be used in a wide variety of applications that may have little to do with the use of porous substrates, per se. For example, ultra high surface area electrical components may have a variety of applications as electrodes for interfacing with, e.g., biological tissue (e.g., in pacemakers), coverings for other biological implants as tissue lattice or anti-infective barriers for catheters, or the like.

In still other applications, porous substrates provide a unique synthesis lattice for providing dense populations of nanofibers/nanowires for use in a variety of different applications, e.g., for use in composite films, etc. Such films may generally be applied as semiconductive composites, dielectric films, active layers for electronic or photoelectric devices, etc.

In still other applications, porous substrates provide a unique synthesis lattice for synthesizing nanofibers, particularly long, unbranched nanowires at high yield and/or density.

A broad range of potential applications exists for these techniques, materials, and articles and will be apparent to one of ordinary skill in the art upon reading the instant disclosure.

II. Articles of the Invention, Structure and Architecture

As noted above, in one aspect, the articles of the invention incorporate porous substrates as a foundation of the article. The porous substrates used in accordance with the present invention typically include any of a variety of solid or semi-solid materials upon which the nanowires may be attached, but through which apertures exist. As such, these substrates may include solid contiguous substrates, e.g., plates, films, or wafers, that may be flexible or rigid, that have apertures disposed through them, e.g., stamped or etched metal or inorganic perforated plates, wafers, etc., porated or perforated films, or the substrate may include aggregates of solid or semisolid components e.g., fibrous mats, mesh screens, amorphous matrices, composite materials, woven fabrics, e.g., fiberglass, carbon fiber, polyaramid or polyester fabrics, or the like. As will be apparent, any of a wide variety of different types of materials may comprise the substrates, including organic materials, e.g., polymers, carbon sheets, etc., ceramics, inorganic materials, e.g., semiconductors, insulators, glasses, including silica based materials (e.g., silicon, $SiO_2$), etc., metals, semimetals, as well as composites of any or all of these.

Additionally, substrates, e.g., rigid or solid substrates, may be engineered to have additional topographies, e.g., three dimensional shapes, such as wells, pyramids, posts, etc. on their surface to further enhance their effectiveness, e.g., provide higher surface areas, channel fluids or gases over them, provide prefiltration in advance of the filtration provided by the porous substrate, per se, etc. Additionally, although referred to as including a porous substrate, it will be appreciated that in application, multiple substrates may be provided together in a single article, device or system. Further, although described and exemplified primarily as planar porous substrates, it will be appreciated that the porous substrates may be fabricated into any of a variety of shapes depending upon the application, including non-planar three dimensional shapes, spheres, cylinders, disks, cubes, blocks, domes, polyhedrons, etc. that may be more easily integrated into their desired application. Substrates, e.g., planar sheet substrates, are optionally rigid or flexible.

Examples of metal substrates include steel/iron, nickel, aluminum, titanium, silver, gold, platinum, palladium, or virtually any metal substrate that imparts a desirable property to the finished article, e.g., conductivity, flexibility, malleability, cost, processibility, etc. In certain preferred aspects, a metal wire mesh or screen is used as the substrate. Such meshes provide relatively consistent surfaces in a ready available commercial format with well defined screen/pore and wire sizes. A wide variety of metal meshes are readily commercially available in a variety of such screen/pore and wire sizes. Alternatively, metal substrates may be provided as perforated plates, e.g., solid metal sheets through which apertures have been fabricated. Fabricating apertures in metal plates may be accomplished by any of a number of means. For example, relatively small apertures, e.g., less than 100 µm in diameter, as are used in certain aspects of the invention, may be fabricated using lithographic and preferably photolithographic techniques. Similarly, such apertures may be fabricated using laser based techniques, e.g., ablation, laser drilling, etc. For larger apertures, e.g., greater than 50-100 µm, more conventional metal fabrication techniques may be employed, e.g., stamping, drilling or the like.

Polymeric and inorganic substrates may be similarly structured to the metal substrates described above, including mesh or screen structures, fibrous mats or aggregates, e.g., wools, or solid substrates having apertures disposed through them. In terms of polymeric substrates, again, the primary selection criteria is that the substrate operate in the desired application, e.g., is resistant to chemical, thermal or radiation or other conditions to which it will be exposed. In preferred aspects the polymeric substrate will also impart other additional useful characteristics to the overall article, such as flexibility, manufacturability or processibility, chemical compatibility or inertness, transparency, light weight, low cost, hydrophobicity or hydrophilicity, or any of a variety of other useful characteristics. Particularly preferred polymeric substrates will be able to withstand certain elevated environmental conditions that may be used in their manufacturing and/or application, e.g., high temperatures, e.g., in excess of 300 or 400° C., high salt, acid or alkaline conditions, etc. In particular, polymers that tolerate elevated temperatures may be particularly preferred where the nanowires are actually grown in situ on the surface of the substrate, as such synthetic processes often employ higher temperature synthetic processes, e.g., as high as 450° C. Polyimide polymers, polyetherketone, polyaramid polymers and the like are particularly preferred for such applications. Those of skill in the art will recognize a wide range of other polymers that are particularly suitable for such applications. Alternatively, lower temperature fiber synthesis methods may also be employed with a broader range of other polymers. Such methods include that described by Greene et al. ("Low-temperature wafer scale production of ZnO nanowire arrays", L. Greene, M. Law, J. Goldberger, F. Kim, J. Johnson, Y. Zhang, R. Saykally, P. Yang, Angew. Chem. Int. Ed. 42, 3031-3034, 2003), or through the use of PECVD, which employs synthesis temperatures of approximately 200° C. In the case where the porous substrate is merely the recipient of nanofibers already synthesized, e.g., where the substrate is either to be coupled to the nanowires or is to act as a macroporous support for the nanowires, a much wider variety of porous substrates may be employed, including organic materials, e.g., organic polymers, metals, ceramics, porous inorganics, e.g., sintered glass, which would include a variety of conventionally available membrane materials, including cellulosic membranes, e.g., nitrocellulose, polyvinyl difluoride membranes (PVDF), polysulfone membranes, and the like.

In some cases, the porous substrate may comprise a soluble material, e.g., cellulose, or the like. Following attachment of the nanofibers, and optionally placement of the overall substrate into its ultimate device configuration, the supporting porous substrate may be dissolved away, leaving behind an interwoven mat or collection of nanofibers. For example, a soluble mesh may be provided with nanofibers attached to its overall surfaces or interior wall surfaces as described herein. The mesh may then be rolled into a cylindrical form and inserted into a cylindrical housing, e.g., a column for separations applications. The supporting mesh is then dissolved away to yield the column packed with nanofibers. Further, as described above, the porous matrix may comprise any of a number of shapes, and be soluble as well, so as to yield any of a variety of shapes of aggregations of fibers, once the substrate is dissolved.

As noted above, the apertures of the substrates used herein typically are defined in terms of their effective pore size or "effective porosity". Although described as apertures or pores, it will be appreciated that the term "aperture" or "pore" when used in the context that it is disposed through a substrate, refers simply to a contiguous pathway or passage through a substrate material, whether that material be a single solid piece of substrate material or a mesh or mat of aggregated pieces of substrate material. Thus, such "apertures" or pores do not need to represent a single passage, but may constitute multiple passages strung together to form the contiguous path. Likewise, an aperture or pore may simply represent the space between adjacent portions of substrate material, e.g., fibers, etc. such that the spaces provide a contiguous path through the material. For purposes of the invention, pore or aperture size, in the absence of any nanofibers disposed thereon, will typically vary depending upon the nature of the application to which the material is to be put.

For example, filtration applications will typically vary pore size depending upon the nature of the particles or other material to be filtered, ranging from tens to hundreds of microns or larger for coarser filtration operations to submicron scale for much finer filtration applications, e.g., bacterial sterilizing filters. Similarly for semi-permeable barrier applications, such pores will typically vary depending upon the type of permissible permeability is sought. For example, breathable moisture barriers may have pore sizes from tens of microns to the submicron range, e.g., 0.2 µm, or smaller. In some cases, it may be desirable to have an effective pore size that is less than 100 nm, and even less than 20 nm, so as to block passage of biological agents, e.g., bacteria and viruses.

The articles and substrates described herein may include nanowires substantially on any and all surfaces of the substrate material including both exterior surfaces and the surfaces that are within the pores. Together, these surfaces upon which nanowires may be disposed are referred to herein as the "overall surface" of the substrate material, while the wall surfaces that are disposed upon the interior walls of the pores are generally referred to herein as the "interior wall surfaces" of the substrate material or pores. As will be clear to one of ordinary skill in reading the instant disclosure, a reference to a surface as an interior wall surface for certain embodiments, e.g., in the case of a fibrous mat or wool like substrate does not necessarily denote a permanent status of that surface as being in the interior portion of a pore or aperture as the basic flexibility and/or malleability of certain substrate materials may provide the ability to shift or move the various portions of the substrate material's overall surface around.

As noted above, the substrates of the invention gain significant unique properties by incorporating nanofibers or nanowires on their surfaces. For most applications, the terms "nanowire" and "nanofiber" are used interchangeably. However, for conductive applications, e.g., where the nanofibers' conductive or semiconductive properties are of interest, the term "nanowire" is generally favored. In either instance, the nanowire or nanofiber generally denotes an elongated structure having an aspect ratio (length:width) of greater than 10, preferably greater than 100 and in many cases 1000 or higher. These nanofibers typically have a cross sectional dimension, e.g., a diameter that is less than 500 nm and preferably less than 100 nm and in many cases, less than 50 nm or 20 nm.

The composition of the nanofibers employed in the invention typically varies widely depending upon the application to which the resulting substrate material is to be put. By way of example, nanofibers may be comprised of organic polymers, ceramics, inorganic semiconductors and oxides, carbon nanotubes, biologically derived compounds, e.g., fibrillar proteins, etc. or the like. For example, in certain embodiments, inorganic nanofibers are employed, such as semiconductor nanofibers. Semiconductor nanofibers can be comprised of a number of Group IV, Group III-V or Group II-VI semiconductors or their oxides. Particularly preferred nanofibers include semiconductor nanowires or semiconductor oxide nanofibers.

Typically, the nanofibers or nanowires employed are produced by growing or synthesizing these elongated structures on substrate surfaces. By way of example, Published U.S. Patent Application No. US-2003-0089899-A1 discloses methods of growing uniform populations of semiconductor nanowires from gold colloids adhered to a solid substrate using vapor phase epitaxy. Greene et al. ("Low-temperature wafer scale production of ZnO nanowire arrays", L. Greene, M. Law, J. Goldberger, F. Kim, J. Johnson, Y. Zhang, R. Saykally, P. Yang, Angew. Chem. Int. Ed. 42, 3031-3034, 2003) discloses an alternate method of synthesizing nanowires using a solution based, lower temperature wire growth process. A variety of other methods are used to synthesize other elongated nanomaterials, including the surfactant based synthetic methods disclosed in U.S. Pat. Nos. 5,505,928, 6,225,198 and 6,306,736, for producing shorter nanomaterials, and the known methods for producing carbon nanotubes, see, e.g., US-2002/0179434 to Dai et al. As noted herein, any or all of these different materials may be employed in producing the nanofibers for use in the invention. For some applications, a wide variety of group III-V, II-VI and group IV semiconductors may be utilized, depending upon the ultimate application of the substrate or article produced. In general, such semiconductor nanowires have been described in, e.g., US-2003-0089899-A1, incorporated herein above. In certain preferred embodiments, the nanowires are selected from a group consisting of: Si, Ge, Sn, Se, Te, B, diamond, P, B—C, B—P(BP6), B—Si, Si—C, Si—Ge, Si—Sn, Ge—Sn, BN, BP, BAs, AlN, AlP, AlAs, AlSb, GaN, GaP, GaAs, GaSb, InN, InP, InAs, InSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag) (Al, Ga, In, Tl, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO, and an appropriate combination of two or more such semiconductors. The nanofibers optionally comprise a gold tip.

In the cases of semiconductor nanofibers, and particularly those for use in electrical or electronic applications, the nanofibers may optionally comprise a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type dopant is selected from a group consisting of: Si, Ge, Sn, S, Se and Te.

In some cases, it may be desirable to utilize nanofibers that have a self sterilizing capability, e.g., in semipermeable bandage, clothing, filtration or other applications. In such cases, the nanofibers may be fabricated from, e.g., TiO$_2$, which upon exposure to UV light oxidizes organic materials to provide a self cleaning functionality (See, e.g., U.S. Patent Application No. 60/468,390, filed May 6, 2003, and incorporated herein by reference in its entirety for all purposes).

Additionally, such nanofibers may be homogeneous in their composition, including single crystal structures, or they may be comprised of heterostructures of different materials, e.g., longitudinal heterostructures that change composition over their length, or coaxial heterostructures that change composition over their cross section or diameter. Such coaxial and longitudinal heterostructured nanowires are described in detail in, e.g., Published International Patent Application No. WO 02/080280, which is incorporated herein by reference for all purposes.

The nanowire portion of the articles of the invention are preferably synthesized in situ, e.g., on the desired surface of the porous substrate. For example, in preferred aspects, inorganic semiconductor or semiconductor oxide nanofibers are grown directly on the surface of the porous substrate using a colloidal catalyst based VLS (vapor-liquid-solid) synthesis method such as those described above. In accordance with this synthesis technique, the colloidal catalyst is deposited upon the desired surface of the porous substrate (which in some cases may include the overall surface of the porous substrate). The porous substrate including the colloidal catalyst is then subjected to the synthesis process which generates nanofibers attached to the surface of the porous substrate. Other synthetic methods include the use of thin catalyst films, e.g., 50 nm, deposited over the surface of the porous substrate. The heat of the VLS process then melts the film to form small droplets of catalyst that form the nanofibers. Typically, this latter method may be employed where fiber diameter homogeneity is less critical to the ultimate application. Typically, catalysts comprise metals, e.g., gold, and may be electroplated or evaporated onto the surface of the substrate or deposited in any of a number of other well known metal deposition techniques, e.g., sputtering etc. In the case of colloid deposition, the colloids are typically deposited by first treating the surface of the substrate so that the colloids adhere to the surface. Such treatments include those that have been described in detail previously, e.g., polylysine treatment, etc. The substrate with the treated surface is then immersed in a suspension of colloid.

Alternatively, the nanofibers may be synthesized in another location and deposited upon the desired surface of the porous substrate using previously described deposition methods. For example, nanofibers may be prepared using any of the known methods, e.g., those described above, and harvested from their synthesis location. The free standing nanofibers are then deposited upon the relevant surface of the porous substrate. Such deposition may simply involve immersing the porous substrate into a suspension of such nanofibers, or may additionally involve pretreating all or portions of the porous substrate to functionalize the surface or surface portions for fiber attachment. A variety of other deposition methods are known, e.g., as described in U.S. patent application Ser. No. 10/673, 092, filed Sep. 25, 2003, and U.S. patent application Ser. No. 10/405,992, filed Apr. 1, 2003, the full disclosures of which are incorporated herein by reference in their entirety for all purposes.

Where nanofibers are desired to be attached primarily to the interior wall portions of the surface of the porous substrate, such deposition may be accomplished by growing the nanofibers in such locations or by selectively depositing the nanofibers in such locations. In the case of in situ grown nanofibers, this may be accomplished by depositing a layer of another material on all of the exterior surfaces of the substrate, e.g., a resist, before depositing the colloids. Following immersion in colloid, the resist layer may be developed and removed to yield substrate having colloid substantially only deposited on the interior wall surfaces of the substrate.

Figure 1B:
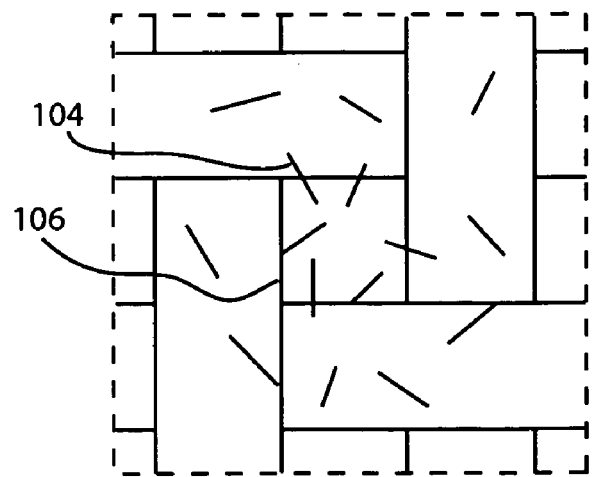

FIGS. 1 and 2 schematically illustrate substrates according to the present invention. In particular, FIG. 1 shows a schematic illustration of a porous nanowire carrying substrate of the invention. As shown in FIG. 1A and 1B, a porous substrate 102 is provided. For purposes of exemplification, a mesh or screen is employed as the porous substrate, although fibrous mats are also useful in such applications. As shown in FIG. 1B, nanofibers 104 are provided that are, at least in part, disposed on the internal wall portions 106 of the apertures or pores, and which extend into the void area 108 of the pores, yielding openings or passages through the overall material that are somewhat more restrictive or narrow than those provided by the underlying substrate, itself. As shown in FIG. 1, the nanofibers 104 are also disposed on other surface portions of the mesh (the overall surface).

Figure 2A:
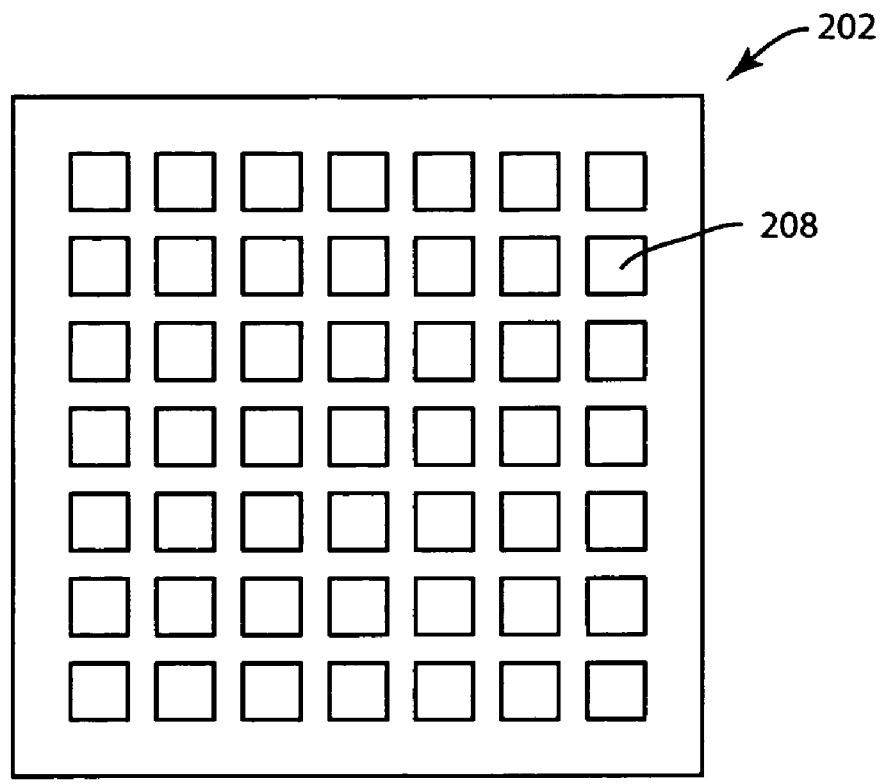
FIG. 2 Panels A and B show a schematic illustration of nanowires attached to the interior wall portions of a porous substrate material.
Figure 2B:
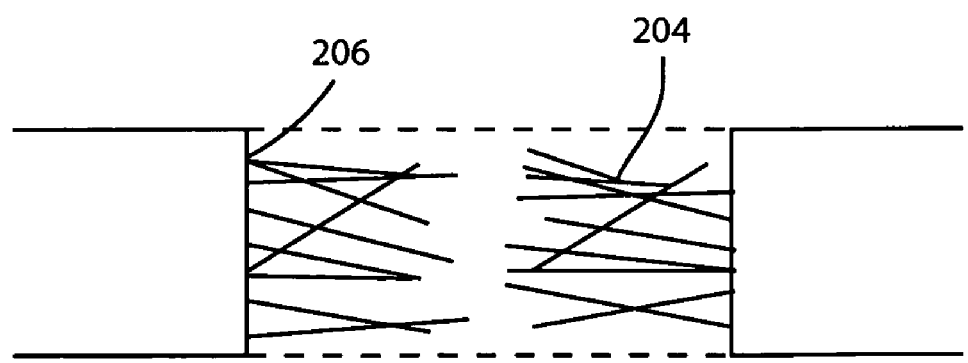

FIGS. 2A and 2B schematically illustrate the case where nanofibers are primarily disposed only on the interior wall portions of the apertures that define the pores. As shown, a perforated substrate 202 forms the underlying porous substrate. A plurality of apertures 208 are fabricated through the substrate 202, e.g., by punching etching or other known fabrication methods. As shown in FIG. 2B, an expanded view of the aperture 208 is provided that details the presence of nanofibers 204 attached to the interior wall portions 206 of the aperture. As shown, the nanofibers generally protrude away from the interior wall surface 206. This is typically accomplished by growing the nanofibers, in situ, using a catalytic growth CVD process, whereupon the fibers grow away from the surface upon which the catalyst is initially deposited. Other methods may also be employed to deposit nanofibers on these interior wall portions that may or may not result in the fibers protruding into the void space of the apertures, including immersing the porous substrate in a suspension of nanofibers that are chemically able to attach to the surfaces of interest.

Figure 12A:
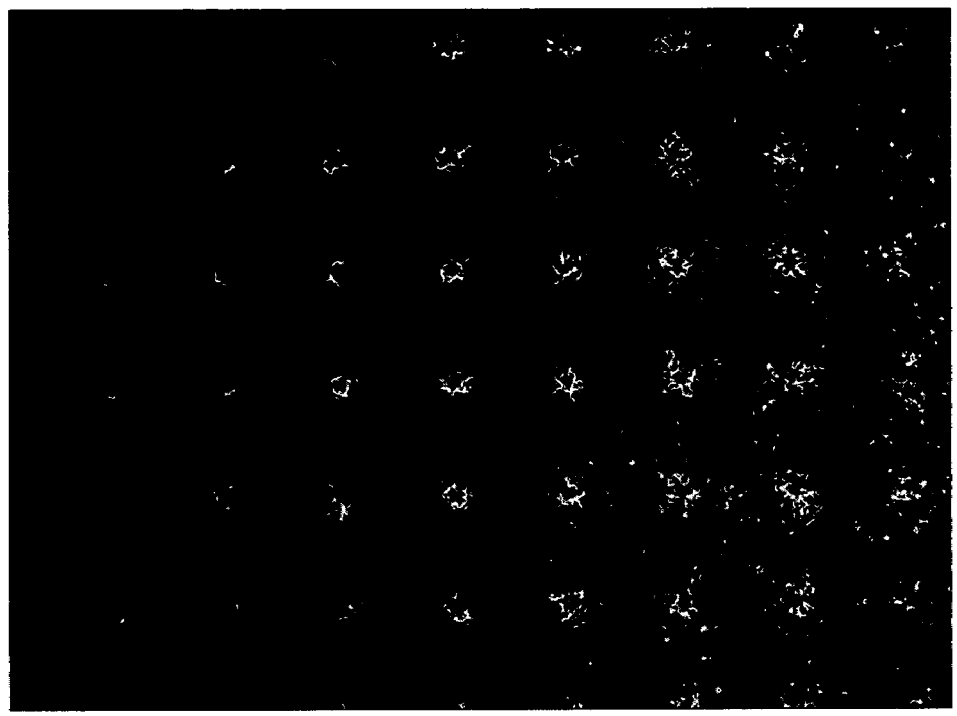
FIG. 12 Panels A and B illustrate an example of the nanofiber bearing, porous substrates of the invention.
Figure 12B:
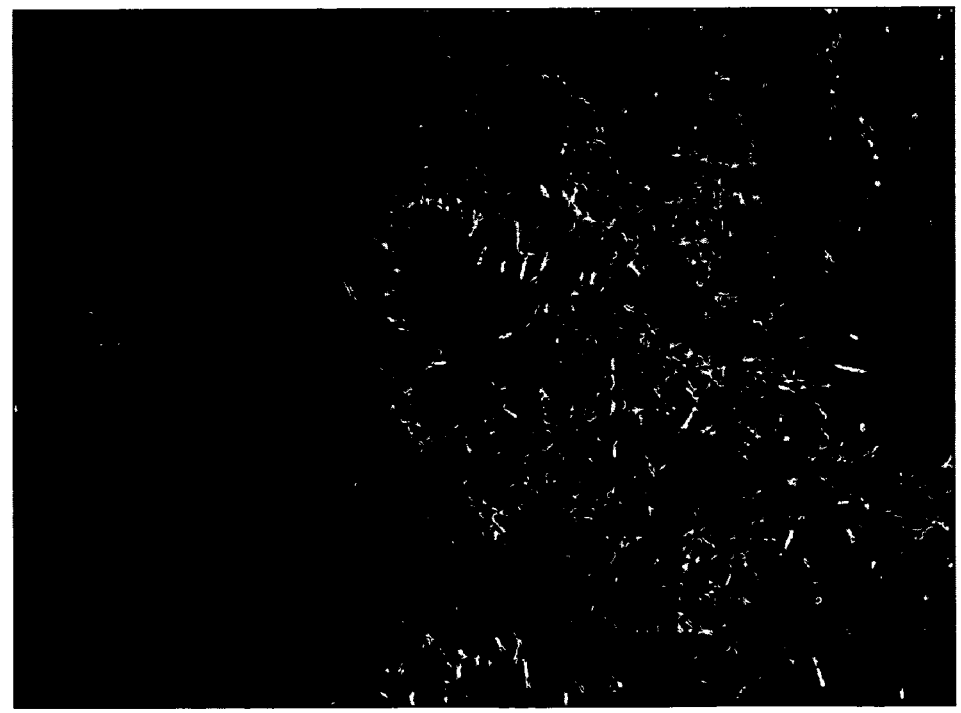

FIG. 12 shows a photograph of a silicon substrate that has pores or apertures disposed through it. Silicon nanofibers were grown over the surface of the substrate, including within the pores. The substrate was a 0.1 mm thick silicon wafer with regularly spaced 100 µm holes disposed through it. FIG. 12A shows a view of a larger area of the substrate, while FIG. 12 B shows a closer up view of the pore and substrate surface, as well as the nanofibers on those surfaces.

In alternative arrangements, the porous substrates may be employed in steps that are discrete from the synthesis process, and that employ the porous substrate as a capture surface for the nanofibers. In particular, nanofibers may be produced as suspensions or other collections or populations of free-standing, e.g., a population of discrete and individual members, nanofibers. Such free standing nanofibers are generally produced from any of the aforementioned processes, but including a harvest step following synthesis whereby the nanofibers are removed from a growth substrate and deposited into a suspending fluid or other medium or deposited upon a receiving substrate, or otherwise moved from a growth or synthesis environment into a manipulable environment, e.g., a fluid suspension. The population of nanowires is then deposited over a porous substrate to yield a mat of deposited nanofibers that form a micro or nanoporous network over the underlying porous substrate. In accordance with this aspect of the invention, the pores in the porous substrate are typically selected so that they are smaller than the largest dimensions of the nanofibers to be deposited thereon, e.g., the length of the nanofiber. For example, where nanofibers in a particular population have an average length of approximately 10 µm, the pores in the substrate will typically be smaller in cross section than 10 µm, e.g., less than 5 µm, less than 2 µm, or smaller. To ensure sufficient capture of nanofibers, the largest cross section of the pore in the porous substrate will typically be less than 50% of the average largest dimension of the nanofiber population, generally the length, in some cases, less than 20% of such dimension, and in many cases, less than 10% of such dimension.

The nanofiber mat is then optionally fused or cross-linked at the points where the various fibers contact each other, to create a more stable, robust and potentially rigid fibrous membrane. The void spaces between the interconnected nanofibers form the porous network of the nanofibrous mat. The effective pore size of the mat will generally depend upon the density of the deposited nanofiber population that is deposited, as well as the thickness of that layer, and to some extent, the width of the nanofibers used. All of these parameters are readily varied to yield a mat having a desired effective porosity.

Figure 9A:
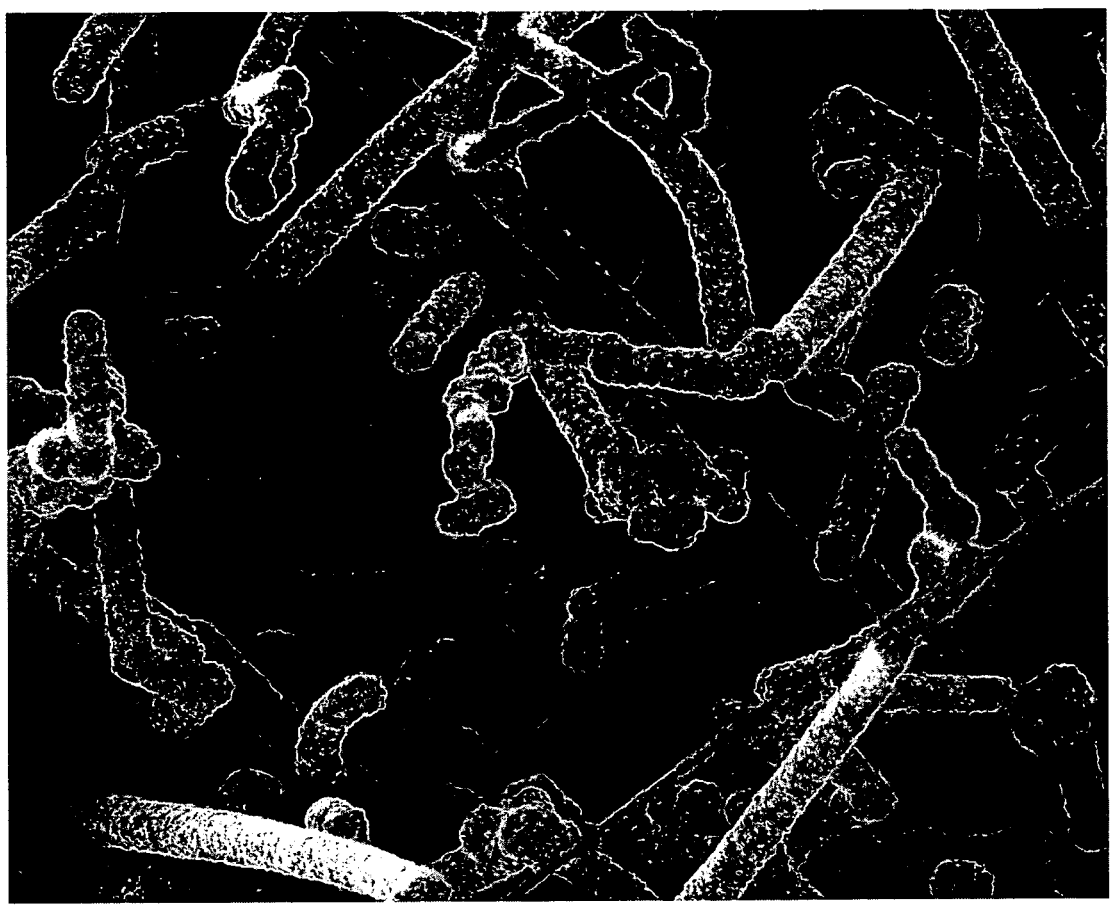
FIG. 9 Panels A and B show electron micrographs of cross-fused or linked nanowires creating an independent mesh network as used in certain aspects of the present invention.
Figure 9B:
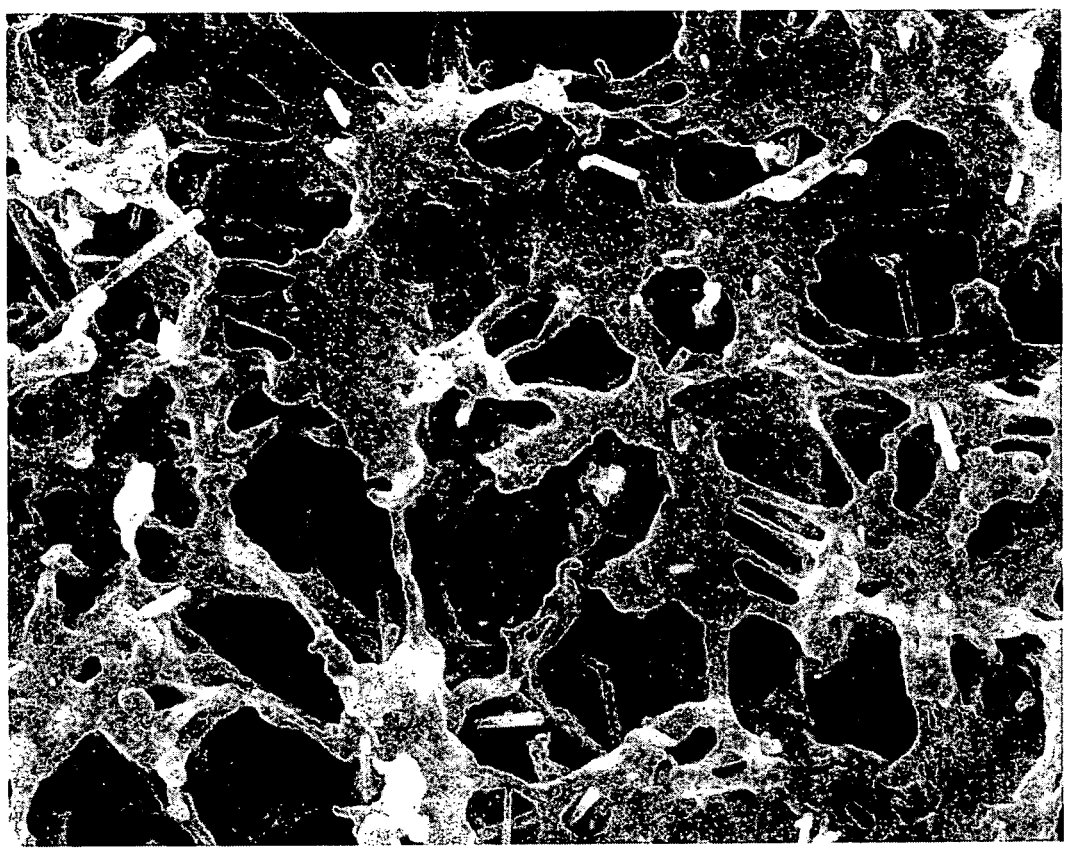

FIGS. 9A and 9B show electron micrographs of cross-linked nanofibrous mats that illustrate certain aspects of the invention. FIG. 9A shows a population of semiconductor nanofibers that were cross-linked through vapor deposition of inorganic material, e.g., silicon. In particular, a population of silicon nanowires was prepared by a conventional synthesis scheme, e.g., silicon nanowires were grown at 480° C., from a gold colloid catalyst, under SiH4 partial pressure, 1 torr, total pressure, 30 torr for 40 minutes. After the growth was terminated by pumping out the process gasses, the temperature of the substrate was ramped up to 520° C. under 30 torr He. The process gases ($SiH_4$) were switched on again once temperature was reached, and the resulting silicon deposition cross-linked the adjacent or contacting nanowires. The deposition time was 10 minutes. As will be appreciated, separately harvested and deposited nanofibers may be similarly crosslinked using this technique.

The nanofibers in FIG. 9B, on the other hand, were linked using a polymer deposition process that at least partially coated or encased the nanofibers to link them together. In particular, a PVDF polymer was suspended along with the nanowires in acetone and sonicated. The acetone was then evaporated to yield the encapsulated or crosslinked nanowires or nanofibrous mat. As can be seen in each case, the network of silicon nanofibers, or nanowires, shows cross-linking at the intersections of various nanofibers. Also as shown, the pores created by the interwoven nanofibers are defined by the void space between the nanofibers.

As noted above, the alternative aspects of the invention may be accomplished by simply depositing nanowires upon a receiving or supporting substrate such that the nanofibers are overlaying each other to form a mat, and preferably a dense nanofiber mat. In general, this process is simplified by using a porous supporting substrate such that the nanofibers may be captured upon the upper surface of the porous supporting substrate while the medium in which the nanofibers were originally disposed is allowed to pass through the pores, essentially filtering the nanofibers with the substrate and densely depositing the nanofibers on the surface of the substrate. The resulting fibrous mat is then treated to crosslink the fibers at the points where they contact or are sufficiently proximal to each other.

Figure 10:
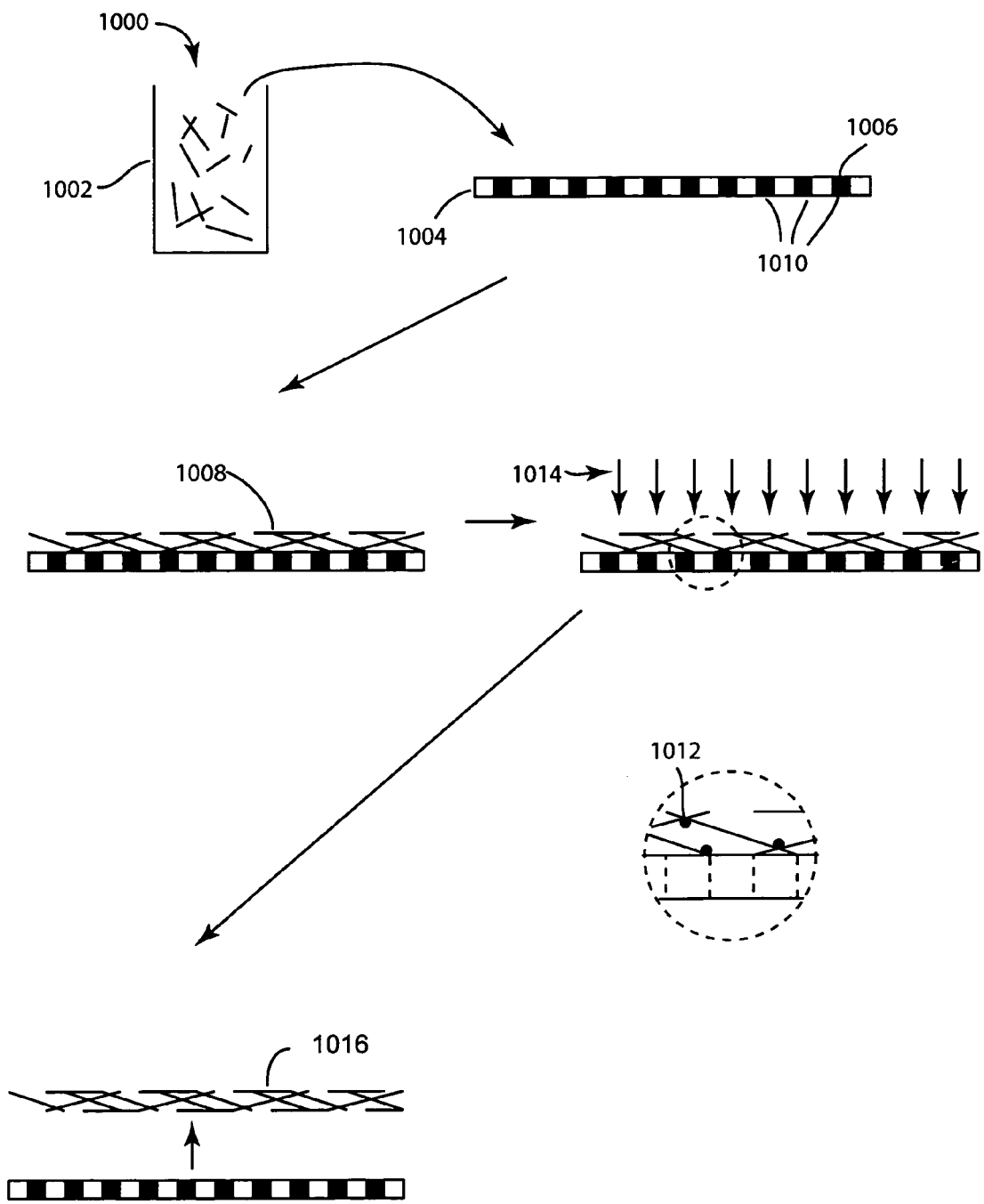
FIG. 10 schematically illustrates a process for producing a cross-linked nanowire mesh network for use either in conjunction with or independent from an underlying porous, e.g., macroporous, substrate.

The process for such mat formation is schematically illustrated in FIG. 10. In particular, a nanofiber population 1000 is provided as a suspension 1002, where the nanofibers may be suspended in liquid, gas, or simply provided as a free flowing population or powder. The nanofiber population is then deposited or poured onto a porous substrate 1004. The nanofiber population 1000 is then retained upon the upper surface 1006 of the porous substrate 1004, at which point it forms an overlaying mat 1008 of nanofibers supported by substrate 1004. The mat 1008 is added to by depositing additional nanofibers onto the substrate. As noted previously, any medium in which the nanofibers are suspended freely passes through pores 1010 in the porous substrate 1004, allowing the nanofibers to pack densely against the upper surface 1006 of the porous substrate 1004.

Once the nanofiber mat 1008 is of the desired thickness and fiber density, the mat may be readily employed upon its supporting macroporous substrate, e.g., as a filter membrane or other semipermeable layer. However, in preferred aspects, the nanofibrous mat is treated (as indicated by arrows 1014) to crosslink the nanofibers at their respective contact points to form couplings 1012 between the nanofibers in the mat, as shown in the expanded view. The use of crosslinked nanofibers has been described for ultra high surface area applications (See, e.g., commonly owned U.S. patent application Ser. No. 10/840,794, filed May 5, 2004, and incorporated herein by reference in its entirety for all purposes). Crosslinking, as noted previously, may be accomplished by a number of means, including thermal fusing, chemical surface modification/crosslinking, encapsulation or coating. Thermal fusing methods may vary depending upon the makeup of the nanofibers, with polymeric nanofibers being fused at substantially lower temperatures than metal or inorganic semiconductor nanofibers.

Nanofibers may also include surface chemical groups that may form chemical crosslinks in order to cross-link the underlying nanofibers. For example, polymeric materials, such as polyacrylamide or polyethylene glycol groups, may be readily coupled to the surfaces of nanofibers, e.g., through well known silane and/or pegylation chemistries. Well known polymer crosslinking techniques are then used to crosslink the nanofibers. Similarly, epoxide, acrylate or other readily available reactive groups may be provided upon the surface of the nanofibers that allow thermal curing, optical curing, e.g., UV, or other chemical interaction and coupling between adjacent, contacting nanofibers to provide the crosslinking.

In another aspect, the nanofibrous mat may be crosslinked together using a polymer coating or encapsulation technique that locks the various nanofibers into position. For example, vapor deposition techniques may be employed to vapor deposit thin polymer layers over the nanofiber portions of the mat, effectively cementing the nanofibers into position. Examples of such polymers include, e.g., PTFE, PVDF, parylene, and the like. A wide variety of other polymeric materials may optionally be employed using a liquid deposition or an in situ polymerization and/or crosslinking techniques, e.g., as described above. As will be appreciated, polymeric crosslinking may provide certain benefits over thermal and/or chemical crosslinking in terms of pliability of the resulting mat of material.

Once the nanofibrous mat is crosslinked, it may be employed along with the underlying macroporous substrate, e.g., as a backing, or it may be separated from the substrate to yield an independent nanofibrous membrane, e.g., membrane 1016. As will be readily appreciated, larger area nanofiber layers may be produced using conventionally available processes, including drum or belt filter techniques where a large area, continuous macroporous substrate layer, e.g., in a belt or as a surface of a drum, is used to retain nanofiber layers, which layers are crosslinked or otherwise treated as described herein. Such processes may be configured in a continuous or large area batch mode operation in order to provide extremely large amounts of the fibrous layer material, e.g., for use in clothing, outdoor fabrics, e.g., tents, and other high volume applications.

In one embodiment, an article of the invention includes a nanofibrous mat that comprises a plurality of overlaid nanofibers, wherein said plurality of nanofibers are crosslinked together at points where such nanofibers contact or are proximal to others of said nanofibers, to form a semipermeable layer. The nanofibrous mat is optionally deposited upon a surface of a porous substrate, with the porous substrate and nanofibrous mat forming a semipermeable layer. At least a portion of the nanofibers optionally comprise an attached hydrophobic moiety.

In one embodiment, methods of producing a contiguous population of nanofibers are provided. In the methods, a porous substrate having an overall surface area is provided, as is a plurality of nanofibers attached to the overall surface area of the porous substrate. A related embodiment also provides methods of producing a contiguous population of nanofibers. The methods include providing a porous substrate having an upper surface and a plurality of pores disposed through the porous substrate, wherein each of said pores has an effective pore size; depositing a plurality of nanofibers onto the upper surface of the porous substrate, said nanofibers having at least one dimension greater than the effective pore size, such that the nanofibers are retained upon the upper surface as a nanofibrous mat; and crosslinking individual nanofibers in the plurality of nanofibers with other individual nanofibers of the plurality of nanofibers to produce a contiguous nanofiber population.

III. Applications

As alluded to herein, the porous substrates of the invention having nanofibers attached to portions of their surfaces have myriad applications that take advantage of a wide variety of particularly interesting properties of such materials. In certain applications, the presence of nanowires provides porous materials with enhanced properties. In other applications, the combination of porous substrates and nanowires provides materials having substantially new properties and usefulness.

A. Semi-Permeable Barriers

In a first particularly preferred application, the porous substrates of the invention are useful as semi-permeable barriers. Semi-permeable barriers, in general, also find a wide variety of different applications depending upon their level of permeability, cost, etc. For example, such barriers may be permeable to gas and not liquid, or to air or gas and not particulate matter. Still further, such semi-permeable barriers may provide antiseptic or antibacterial properties to their applications.

In one aspect, the invention provides a semipermeable membrane including a porous substrate having a plurality of apertures disposed therethrough, the porous substrate having an overall surface that includes an interior wall surface of the apertures, and a plurality of nanofibers deposited upon or attached to at least a portion of the overall surface of the porous substrate, wherein the nanofibers and apertures together define a pore through the semipermeable membrane, the pore being permeable to one or more materials and not permeable to one or more different materials. The nanofibers can be attached to or deposited on at least a portion of the overall surface of the porous substrate. Individual nanofibers can be crosslinked with other individual nanofibers to provide a crosslinked nanofibrous mat on the surface of the porous substrate. The nanofibers optionally comprise a hydrophobic moiety coupled thereto, rendering the pore permeable to gas but not permeable to liquid water. The pore can have an effective pore size that excludes particles of a first particle size while permitting passage of particles of a second particle size, smaller than the first particle size. The effective pore size can be, e.g., smaller than 10 μm, smaller than 1 μm, less than 0.2 μm, less than 100 nm, or even less than 20 nm. The membrane can be incorporated into a variety of articles. For example, a filter cartridge can include a semipermeable membrane of the invention disposed within a housing having an inlet passage in fluid communication with a first side of the semipermeable membrane and an outlet side in fluid communication with a second side of the semipermeable membrane. In one embodiment, the housing is coupled to a breathing mask to filter breathing air. As another example, an article of clothing can include a semipermeable membrane of the invention, e.g., layered with at least a second fabric layer.

1. Filtration

In their simplest aspect, semi-permeable barriers are used as filtration media for separating gases or liquids from particulate matter. For example, there are a wide range of different filtration options available for e.g., air filtration, from simple consumer filtration needs, e.g., home furnaces, air conditioners, air purifiers, to more demanding filtration needs, e.g., HEPA filtration for industrial use, hazardous materials filtration for protective gear, clean room applications, automotive applications, etc. For liquid applications, such filters may provide water purification, particulate separation for fuels and lubricants for industrial or consumer machinery, e.g., automobiles, etc.

In accordance with the filtration applications of the present invention, porous substrates are used as the foundation for the filtration media to be produced. Nanofibers are then provided on the surfaces overall or substantially only interior surfaces to further enhance the filtration capabilities of the underlying porous foundation. In particular, one of the key areas that are sought for improvement in filtration media is the ability to increase the filtration efficiency, e.g., reduce the pore size or increase the overall capacity/lifetime of a filter, without yielding a substantial increase in the pressure drop, which could lead to early filter failure/clogging, higher energy demands, etc.

The enhancements brought by the present invention include effectively decreasing the pore size of the filter without substantially increasing the pressure drop across a filter. In particular, the present invention provides porous substrates having nanofibers disposed within the pores of the substrate to provide additional filtration by modifying the effective pore size. Nanofibers, because of their extremely small size, are particularly useful in these applications due to their ability to substantially increase the surface area within a pore without substantially increasing the volume of material disposed within that pore, this increasing the filtration efficiency without decreasing the flow through the filter media. Fluids or gases are then passed through the porous substrate to separate particulate materials from the carrier liquid or gas.

Figure 3A:
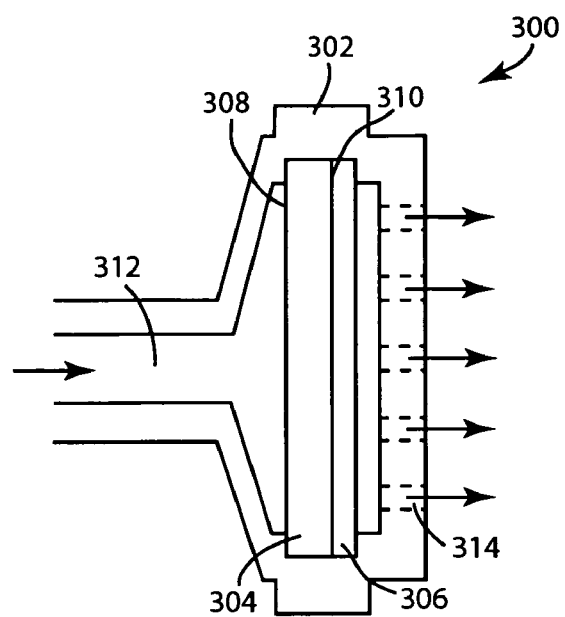
FIG. 3 Panels A and B show a schematic illustration of the articles of the invention incorporated in a filtration cartridge.
Figure 3B:
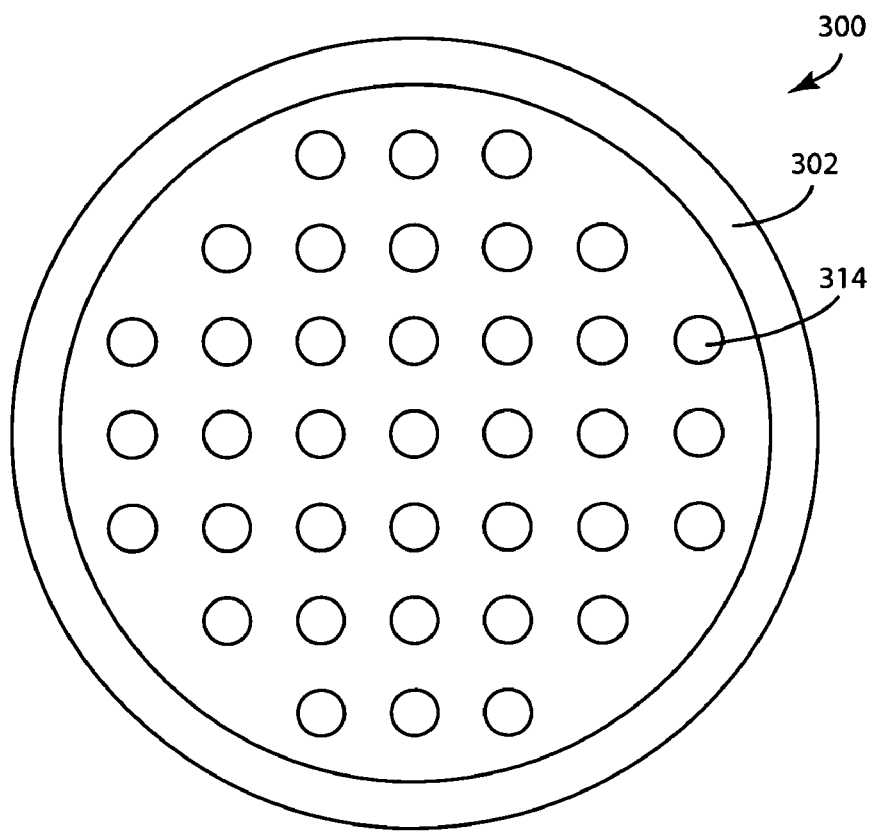

One example of a filtration cartridge, e.g., for a filter mask, gas line or the like, is illustrated in FIGS. 3A and 3B. As shown in FIG. 3A, a filter cartridge 300 includes a main housing 302 having a filter layer 304 disposed within the housing. A filter support 306 is typically also included on the low pressure side of the filter layer to provide structural support to the filter layer. The filter layer typically includes an inlet or high pressure side 308 and a low pressure or outlet side 310. Gas or liquid is filtered through the cartridge by passing from the high pressure or inlet side to the low pressure or outlet side of the filter. The filter cartridge thus includes an inlet passage 312 or passages for passing gas or fluid to the inlet side of the filter layer to be filtered, and an outlet passage 314 or passages for passing gas or fluid that has been filtered through the filter layer 304. Filter 3B shows an end view of the outlet side of the particular filter cartridge shown in FIG. 3A.

As noted, the filtration cartridge may be incorporated into larger systems depending upon the ultimate application. For example, air filters may be incorporated into heating and air conditioning or other environmental control systems to provide purified air for, e.g., commercial or industrial, i.e., clean room, applications. Filtration cartridges of the invention may optionally be incorporated into fluid filtration systems as well, for water, fuel or chemical filtration applications.

In accordance with the filtration applications, effective pore sizes of the filter media may be varied depending upon application, e.g., from coarse particle filtration, e.g., effective pore sizes of 1, 10 or more microns, to antibacterial filtration, e.g., effective pore sizes of 0.2 μm or less, e.g., down to 20 nm or less. As alluded to elsewhere herein, the phrase "effective pore size" does not necessarily reflect the size of a discrete passage through the substrate, but instead may reflect the cross sectional dimensions of a contiguous path through which fluid, gas or particles may pass, or be blocked from passing. In addition, the "effective pore size" of a given passage does not necessarily define the absolute dimensions of the contiguous passage, but instead defines the size of the particles that are effectively blocked from passing through the passage. Typically, such varied pore sizes will be of a function of nanowire density disposed within the larger apertures that exist in the underlying substrate, the diameter and length of the nanofibers, as well as a result, to some extent, of the size of such apertures to begin with.

Similarly, the composition or make up of the filtration media, both in terms of nanofibers and the underlying substrate, may depend upon the application to which the material is to be put, with materials being generally selected to withstand the conditions to which they will be exposed. Such conditions might include extremes of temperature, alkalinity or acidity, high salt content, etc.

In one aspect the invention includes methods of filtering a fluid or gas. In the methods, a porous substrate is provided and the gas or liquid is passed through the porous substrate to filter the gas or liquid. The substrate has a plurality of apertures disposed therethrough to provide a porous substrate that has an overall surface area that includes an interior wall surface area of the apertures, and the substrate comprises a plurality of nanowires attached to at least a portion of the overall surface area of the porous substrate.

2. Breathable Moisture Barriers

In a related aspect, the substrate is configured to be permeable to gas, e.g., air, while remaining impermeable to liquid. For example, such barriers are particularly useful as breathable moisture barriers for clothing and medical applications, allowing moisture vapor, oxygen and other gases to pass through the barrier freely, but preventing liquid from passing. In accordance with the invention, this is accomplished by providing nanofibers within the apertures that are disposed through the porous substrate. In contrast to other aspects of the invention, however, the nanofibers for the moisture barrier applications are selected or treated to have increased hydrophobicity. Treatment of nanofibers surfaces to increase hydrophobicity was described in detail in U.S. Patent Application No. 60/466,229, filed Apr. 28, 2003, which is hereby incorporated herein by reference in its entirety for all purposes. In particular, the nanofibers and or the substrate surface may be derivatized to attach hydrophobic chemical moieties to their surfaces to increase the hydrophobicity of the material. Those of ordinary skill in the art are well versed in the coupling of hydrophobic chemical moieties to substrates, including, e.g., silane chemistries for treating silica based substrates, and the like. By providing such super hydrophobic nanofiber surfaces on porous underlying substrates, one can prevent passage of liquids, e.g., liquid water or other aqueous solutions, while permitting air, water vapor or other gases to pass. Typically, such barriers will be substantially impermeable to moisture, e.g., preventing passage of the substantial majority of moisture that comes into contact with the surface under ambient conditions.

Figure 4A:
FIG. 4 Panels A and B show a schematic illustration of a layered textile that incorporates a substrate of the invention as a semi-permeable moisture barrier for use in, e.g., outdoor clothing.
Figure 4B:
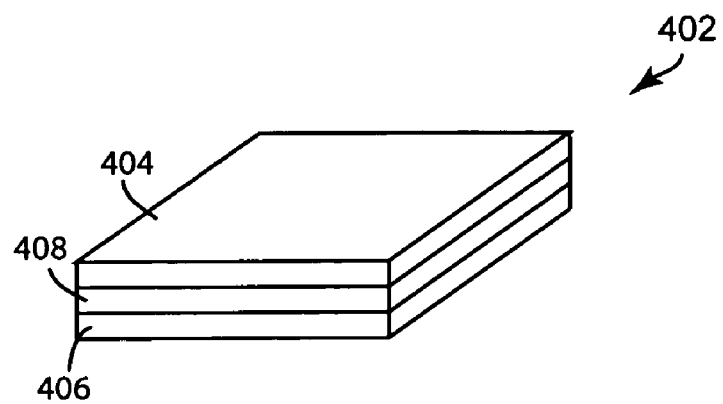

Such moisture permeable barriers are particularly useful in outdoor gear, such as clothing, shelters, etc. where it is desirable to eliminate moisture generated from within, while not permitting liquid water to enter. FIGS. 4A and 4B schematically illustrate a layered textile product, e.g., coat 400, that is comprised of a layered textile 402 (shown in exploded view in FIG. 4B). As shown, a layer of the porous nanofiber bearing substrate material 408 is provided between layers of other material, e.g., a nylon outer shell 404 and cotton or polypropylene fabric lining 406, which provides external protection from wind and cold and internal comfort against the skin or clothing of the wearer.

In one aspect the invention includes methods of producing a gas permeable moisture barrier. In the methods, a porous substrate that comprises a plurality of apertures therethrough and a plurality of nanofibers attached to at least a portion of an overall surface area of the porous substrate are provided. The porous substrate and nanofibers together provide a gas permeable barrier. At least the nanofibers are treated to increase hydrophobicity of the nanofibers attached to the overall surface of the porous substrate, to provide a gas permeable moisture barrier.

3. Bandages

In another preferred embodiment, these moisture permeable barriers are useful as bandages or wound dressings, as they allow oxygen to reach wound areas, gas and vapor to escape wound areas, all the while preventing liquid water and other harmful forces/abrasions, etc., from contacting the wound areas. In addition to their benefits as semi-permeable barriers, the nanofiber coated surfaces also may provide adhesion, to maintain the bandage in place, e.g., adhering the bandage to itself or the skin around the wound area. Use of nanofiber surfaces as dry adhesives or high friction materials is described in detail in U.S. patent application Ser. No. 10/661,381, filed Sep. 12, 2003, and incorporated herein by reference in its entirety for all purposes. Additionally, such nanofiber coatings may comprise antimicrobial materials, e.g., ZnO or the like, to help prevent any infections in the wound areas.

Figure 5A:
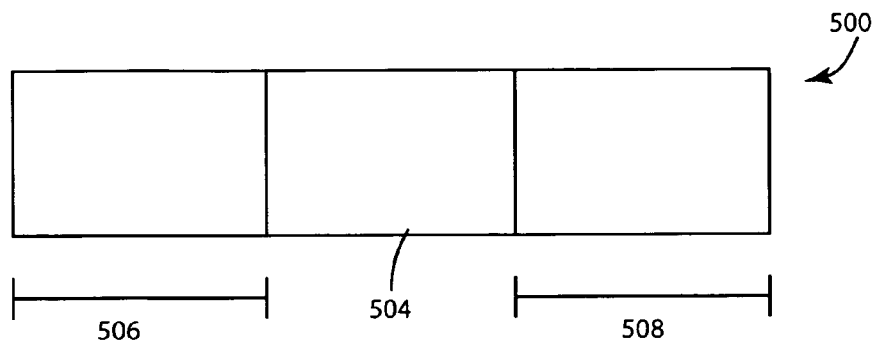
FIG. 5 Panels A and B show a schematic illustration of the articles of the invention incorporated in a self adhesive, moisture repellant bandage.
Figure 5B:
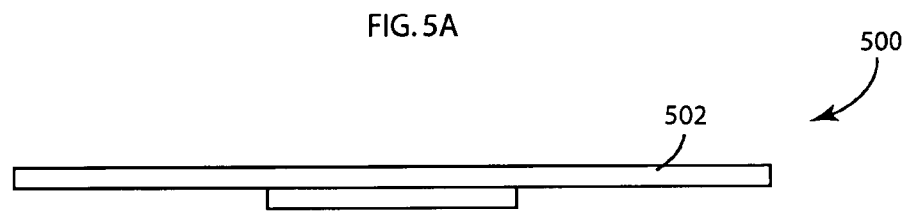

FIG. 5 schematically illustrates a self adhesive, semi permeable, moisture repellant bandage as described above. As shown, a bandage 500 includes a flexible porous substrate strip 502 of the invention, e.g., a woven fabric or soft mesh material, i.e., a polymer or cloth mesh, having nanofibers that are appropriately treated to provide a hydrophobic barrier, e.g., a moisture barrier (represented by hatching on strip 502). The substrate strip 502 functions both as a breathable moisture impermeable cover and as an adhesive strip. A protective pad 504 is provided upon a portion of one side of the substrate strip 502 to provide protection for a wound that is covered by the bandage. When applied to a wound, the protective pad overlays the wound to provide protection from rubbing or other contact, while the portions 506 and 508 of the strip provide adhesion to the surface tissues adjacent a wounded area (or when wrapped completely around a wounded appendage, to an opposing surface of the other end of the substrate strip, e.g., region 506 adheres to the back side of region 508).

B. Vapor Barriers

In a related aspect, the porous substrates of the invention are useful in breathable chemical/biological protective clothing and apparatus, to adsorb or decompose various organic and inorganic vapors. In accordance with the vapor barrier applications of the present invention, porous substrates (e.g., fabrics or flexible meshes) are used as the foundation. Preferably, an activated carbon fabric is used. The activated carbon fabric absorbs organic vapors and acts as a support structure. Activated carbon fabric is commercially available, e.g., from Spectracorp.

Nanofibers (e.g., silicon nanowires, carbon nanotubes, or polymeric nanofibers) are embedded, disposed on, or grown in situ on the activated carbon fabric or other substrate. The nanofibers reduce the permeability of the activated carbon fabric such that adsorption of vapors is more efficient, permitting the layer to be thinner. A hydrophilic surface is optionally present on the nanofibers (e.g., due to the nanofiber composition or to surface treatment of the nanofibers with a hydrophilic material), such that a high degree of moisture vapor transmission can be maintained through the layer despite the reduced air permeability.

The nanofibers are functionalized with moieties that bind or decompose vapors. For example, the nanofibers can be functionalized with moieties that bind or decompose non-organic gases such as phosgene which are not absorbed by activated carbon. The nanofibers can be functionalized with a chemical moiety, e.g., a chemical moiety that absorbs or decomposes a non-organic gas, such as a carboxylic acid moiety which binds ammonia or a moiety selected from Table 1. In a preferred aspect, the nanofibers are functionalized by attachment of nanocrystals to the nanofibers. The nanocrystals can comprise a material such as Ag, ZnO, CuO, $Cu_2O$, $Al_2O_3$, $TiO_2$, MgO, FeO, $MnO_2$, Zn, or a material selected from Table 1, for example. Multiple functionality can be conveniently imparted by using nanocrystals of different compositions, attaching two or more populations of nanocrystals or other nanostructures comprising different materials adsorbing or binding different gases to the nanofibers (e.g., two, three, four, five, six, or more populations). In a related aspect, two or more batches of nanofibers can be chemically derivatized, mixed, and incorporated into the fabric. Similarly, two or more populations of nanofibers can be synthesized from different materials, e.g., selected from Table 1, mixed, and incorporated into the fabric (with or without additional functionalization), or nanofiber longitudinal heterostructures (where a single nanofiber comprises two or more materials) can be used. In a related aspect, nanocrystals or other nanostructures can be attached to a mesoporous carbon fabric or other fabric, particularly another high surface area fabric, even in the absence of nanofibers.

A nanocrystal generally denotes a structure that is substantially monocrystalline (or the core of which is substantially monocrystalline). Nanocrystals typically have a diameter that is less than 500 nm and preferably less than 100 nm or 50 nm and in many cases, less than 20 nm or 15 nm. Nanocrystals optionally have an aspect ratio of less than 10, for example, less than 5 or 2, and in some cases, between about 0.1 and about 1.5. Exemplary nanocrystals include, but are not limited to, substantially spherical nanocrystals (e.g., spherical nanocrystals having a diameter between 1 nm and 6 nm), rod shaped crystals (e.g., rods that are about 5×50 nm), and tetrapods (also called nanotetrapods, which have four rod-like arms coming out of a central core). Techniques for chemically modifying nanofibers and/or attaching nanocrystals the nanofibers are well known in the art; for example, coating the nanofibers with polylysine or a polymer. Attachment can be covalent or noncovalent.

Figure 13:
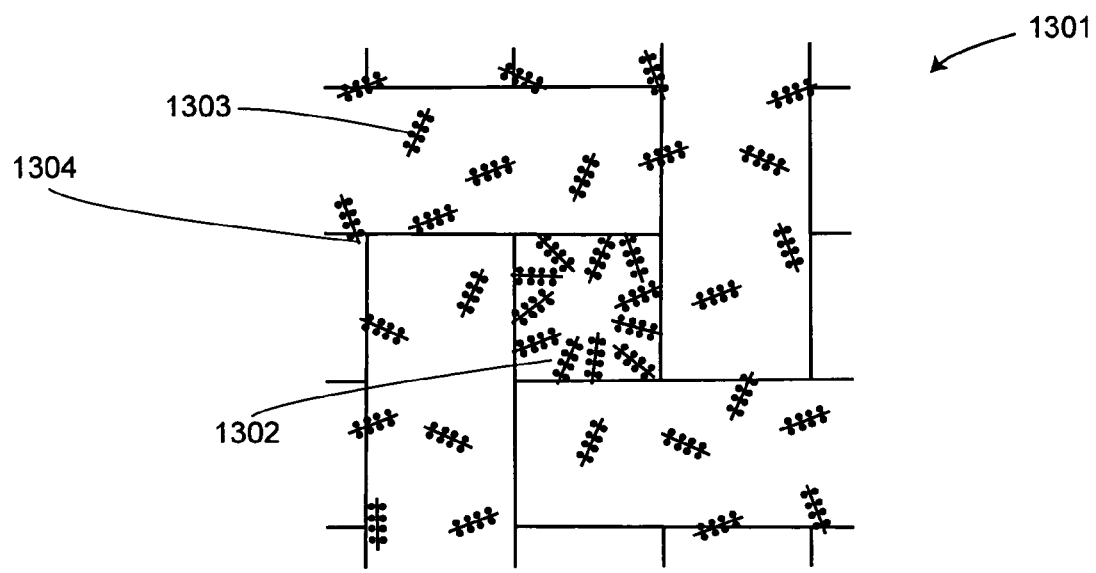
FIG. 13 schematically illustrates a nanofiber-enhanced fabric for use, e.g., in protective clothing or apparatus.

FIG. 13 schematically illustrates a nanostructure-enhanced fabric as described above. As shown, woven fabric 1301 includes apertures 1302. Nanofibers 1304 are attached to the surface of the fabric, and nanocrystals 1303 are attached to the nanofibers.

The fabric or other substrate can be incorporated into an article of clothing, for example, a protective suit, or into other protective apparatus. The nanofiber-enhanced fabric is optionally protected by application of a layer of porous fabric or other porous material on one or both sides.

The vapor-absorbing fabrics of the invention offer a number of advantages over current protective layers. For example, chemical/biohazard protection suits for the U.S. military are currently based on activated carbon pellets embedded in a urethane polymer. Although the pellets absorb many hazardous vapors, the suits have a low moisture vapor transmission rate and are susceptible to many non-organic vapors. Due to its extremely high surface area and high binding affinity for organics, activated carbon cloth has been used commercially in hazardous protection suits. However, the weakness of these fabrics is their inability to absorb non-organic molecules. By filling in the interstices of the fabric with nanofibers that are functionalized to decompose or absorb the non-organic vapors, a single layer fabric such as those described above can provide full functionality while maintaining good moisture vapor transmission.

TABLE 1

Exemplary materials for functionalization of nanofibers.

| Absorber/Decomposer | | Chemical Warfare Agents | Toxic Industrial Compounds | | |
|---|---|---|---|---|---|
| Name | Compound form | | Inorganic Acid Gasses | Organic | Biological |
| Aluminum Oxide | $Al_2O_3$ | Ammonia, VX, GD, HD, Simulants: 2CEES, DMMP | $SO_2$ | 4-Vinylpyridine, p-Cresol | |
| Titanium Dioxide | $TiO_2$ | Ammonia, HCl, VX, GD, HD, Simulants: 2CEES, DMMP, Paraoxon | | Formaldehyde, Nicotine, p-Cresol | |
| Magnesium Oxide | MgO | Ammonia, HCl, VX, GD, HD, Simulants: DMMP, Paraoxon | $SO_2$, $CO_2$ | Acetaldehyde, 4-Vinylpyridine, Formaldehyde, Nicotine | Antimicrobial/biocidal ($MgO*I_2$, $MgO*Cl_2$) |
| Copper Oxide, Cu Salts | $Cu_2O$, CuO, $CuSO_4*5H_2O$, $CuCl_2*2H_2O$, $Cu(NO_3)_2*3H_2O$ | Ammonia, Phosgene, HCN, Chlorine, Arsine | $H_2S$, $SO_2$, $NO_2$ | | |
| Zinc Oxide, Salts | ZnO, $Na_2ZnO_2$, | Paraoxon, Ammonia, Phosgene, HCN, Arsine | $H_2S$ | | Antimicrobial/biocidal |
| Silver, Silver Oxide, Ag Salts | Ag, Maglon, $Ag_2O$, Surfacine, $AgNO_3$ | Arsine, Phosphine, Phosgene, Chlorine, Diphosgene | | | Antimicrobial/biocidal |
| Iron Oxides | FeO, $Fe_2O_2$ | | $H_2S$ | Mercaptans ($CH_3SH$), Dimethyt Sulfide, Halogenated Hydrocarbons | |
| Manganese Oxide, Salt | $MnO_2$, $Mn_xO_y$, $KMnO_4$ | | CO (w/ CuO), $NO_2$, $H_2S$ | Aldehydes | |
| Chromium Salts | $CuCrO_4$, $CuCrO_4*NH_3*5H_2O$, $Na_2Cr_2O_7$, $(NH_4)2Cr_2O_7$ | Cyanogen Chloride (ClCN) | $NO_2$, $H_2S$ | | |

TABLE 1-continued

Exemplary materials for functionalization of nanofibers.

| Absorber/Decomposer | | Chemical | Toxic Industrial Compounds | | |
|---|---|---|---|---|---|
| | | | Inorganic Acid | | |
| Name | Compound form | Warfare Agents | Gasses | Organic | Biological |
| Polyoxometallates (POMs) | H5PV2Mo10O40 type heteropoly acids, PW9O37 | GD, HD | | | |
| Sulfur | | | Mercury | | |
| Potassium Salts | $K_2CO_3$, KI, $K_2MnO_4$ | Phosphine, Arsine | $SO_2$, $NO_2$, $H_2S$, Carbon Disulfide, Mercury | Methyl Iodide (radioactive) | |
| Phosphoric & Sulfuric acid | $H_3PO_4$, $H_2SO_4$ | Ammonia | Mercury | Amine, Acetaldehyde | |
| Pyridine | $C_5H_5N$ | Cyanogen Chloride | | | |
| Triethylenediamine (TEDA) | | | | Methyl Iodide (radioactive) | |
| Para-Aminobenzoic acid (PABA) | | | $H_2S$ | | |
| Ortho-Iodosobenzoic acid BA | | GB, GD, GA, simulant Dimebu | | | |

C. High Contact Surface for, e.g., Electrical Interfacing

As alluded to previously, the above described applications typically employ nanofibers disposed upon a porous substrate to provide enhanced properties to the porous substrates, e.g., enhanced porosity for filtration, moisture repulsion, etc. However, in a number of applications, applying nanofibers to a porous substrate provides a unique material that is not employed simply for its porosity, but for other properties that are enhanced by the synergistic structural characteristics of small dimension materials coupled to a high surface area underlying substrate.

In particular, application of nanofibers to a porous substrate, as a result of its higher surface area, provides for higher packing levels of nanofibers per square centimeter of projected area. In particular, dense mats of nanofibers may be provided joined together on the porous substrate, which density levels would not be readily achieved on flat surfaces. The higher surface area of nanofibers is also readily accessible via the apertures or pores in the underlying substrate.

In addition to the increase in nanofiber densities and/or higher surface areas, porous substrates, e.g., meshes and fibrous mats, tend to be flexible by comparison to more rigid, solid substrates, e.g., silicon wafers, metal plates, or the like. Additionally, depending upon the relative porosity of the substrate, the overall article may benefit from being partially or even substantially translucent or transparent, e.g., like a window screen.

D. High Surface Area/High Density Fiber Applications

Separate and apart from the properties set forth above, porous substrates can also provide a lightweight, high density lattice for maintaining, handling, storing and otherwise using nanofibers. Nanofibers may be harvested from this lattice, or portions of the lattice may be used in their entirety to be applied in more nanofiber specific applications, e.g., as semiconductive elements, composite filler materials for structural or electrical enhancement, high surface area matrices, e.g., for separations, or the like.

In still other applications, the porous substrates having nanowires disposed thereon may provide electrical integratability to the nanofibers (or in this case, specifically nanowires) that are attached thereto. Specifically, use of conductive porous substrates may provide at least a portion of the electrical connection to the nanowires necessary for the given application. For example, semiconductor nanowires coupled to a metallic or other conductive or semiconductive mesh are already partially integrated into an electrical circuit, e.g., the mesh becomes an electrode, e.g., source or drain, in the overall device.

The following description includes a number of such specific examples of applications that benefit from the aforementioned properties for illustration purposes alone. However, a much larger number of specific uses and applications of the substrates and articles of the invention will be readily apparent to those of skill in the art upon the realization of the above-described benefits, and the following description should not be viewed as limiting and in no way excludes such applications.

In a first exemplary application, the substrate of the invention is used as one electrode in a diode configuration. In particular, a conductive mesh is used as the underlying porous substrate with nanowires attached to its surfaces, e.g., overall surface. The composition of the mesh is selected to have a work function that promotes conduction of the major carriers in the nanowire portion. For its part, the nanowire portion is selected to provide one half of the diode circuit, and may include, e.g., p doped nanowires. In accordance with this architecture, the nanowire coated porous substrate functions as a portion of the diode circuit. The other portion of the diode circuit may be provided as either a conventional semiconductor substrate or as a mirror image of the first, except with the materials being selected to conduct the other carriers, e.g., holes, e.g., by providing n-doped nanowires and appropriate electrode compositions for the underlying substrate. The two substrates are then mated to interface the nanowires at the surface to provide the functioning diode. Additional elements may also be provided to ensure proper contact between the nanowires, including conductive elements, annealing steps, etc.

In another exemplary application, high surface area nanowire coated substrates may be used as electrodes for interfacing with other elements, e.g., electrical or non-electrical, such as human tissue for electrical stimulation of the tissue. By way of example, electrodes for pace makers typically benefit from having high surface areas, and thus making more complete contact to the tissue they are stimulating. Relatedly, where the nanofiber coated article is being used as a tissue lattice, e.g., to facilitate bioincorporation, higher surface areas and greater porosity are highly beneficial in providing adherence points without blocking access to such tissue by nutrients etc. Specifically, as described in U.S. Patent Application No. 60/468,390, filed May 6, 2003, nanofiber coated surfaces on medical implants provide 'non-tortuous path' enhanced surface areas that can provide enhanced tissue adhesion and bioincorporation. It is expected that by providing such nanofiber surfaces over porous underlying substrates, these properties will be further enhanced.

In a particular application, such a diode arrangement is employed as a photoactive element, e.g., as a photovoltaic or photodiode device. The use of partially or substantially translucent porous substrates facilitates this application in letting light pass through the electrode components to impinge on the semiconductor nanowires, thus generating charge separation at the heterojunction of the opposing nanowires. Selection of materials for the opposing underlying substrates may follow the same criteria as used in conventional photovoltaic devices. For example, one underlying substrate mesh may be comprised of aluminum while the other is comprised of another metal having a different work function, e.g., ITO, or a similar conductive material.

Previously described nanocomposite photovoltaics have employed an active layer of a nanocomposite material sandwiched between two conductive layers that function as electrodes. The upper electrode typically comprises a transparent conductive coating on the active layer, e.g., indium tin oxide (ITO). These nanocomposite photovoltaic devices employed a first component in which initial charge separation occurs. This typically employed a nanocrystal in which an exciton was created upon exposure to light. This nanocrystal component typically conducts one charge carrier better than the other, e.g., electrons. The nanocrystals are typically disposed in a matrix of another material which conducts the other charge carrier, e.g., holes, away from the nanocrystal component. By conducting the two carriers to opposite electrodes, one generates an electric potential. Typically, the hole conducting component comprises an organic semiconducting polymer, e.g., poly-3-hexylthiophene (P3HT), although the hole conducting component can be another nanocrystal of a different composition. The overall architecture of a nanocomposite photovoltaic device is described in detail in, e.g., U.S. patent application Ser. No. 10/656,802, filed Sep. 4, 2003.

Figure 6A:
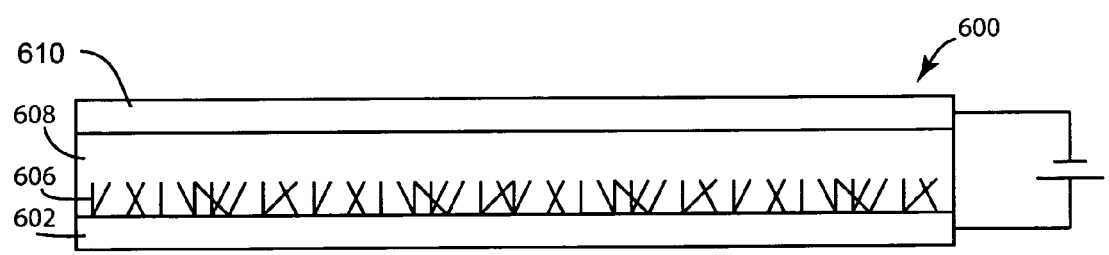
FIG. 6 Panels A and B are schematic illustrations of the substrate material of the invention incorporated into a photovoltaic device.
Figure 6B:
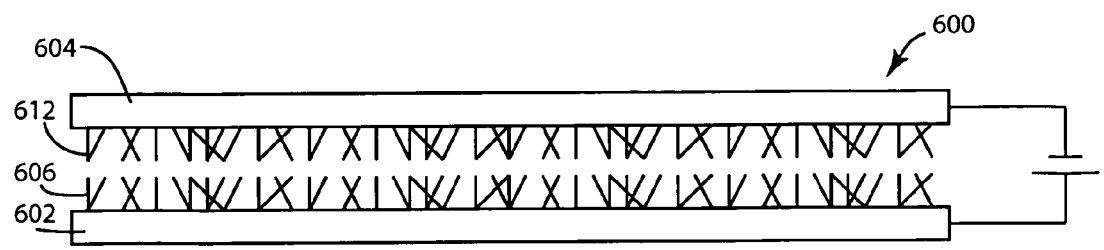

In accordance with the present invention, the overall photovoltaic device 600 includes one (as shown in FIG. 6A), or two (as shown in FIG. 6B) porous substrates 602 and 604 upon which semiconducting nanowires are deposited. The first porous substrate 602 typically comprises a first conductive mesh 602a or other porous material (as described previously herein) that functions as one electrode in the system, e.g., the lower electrode, and includes a first population of nanowires 606 of a first composition attached to its overall surfaces. In a first embodiment shown in FIG. 6A, the first porous substrate 602 and its associated nanofibers are coated with a conductive matrix material 608 that has a type-II band gap offset from the nanowire population 606, so as to affect charge separation. A transparent electrode 610 is then provided over the matrix layer 608.

In a second exemplary embodiment, the upper, transparent electrode 610 in FIG. 6A is replaced by the second porous substrate 604, which is again fabricated from a conductive mesh 604a, but which includes a different work function from that of the first porous substrate 602, to facilitate charge separation. A second population of nanowires 612 is provided attached to the second porous substrate 604. The composition of the first and second nanowire populations 606 and 612, respectively, is selected to provide a type-II bandgap energy offset, again, so as to facilitate charge separation and differential conduction. The first and second porous substrates (602 and 604) are then mated together such that their respective nanowire populations 606 and 612, respectively, are in electrical communication so as to permit charge separation between the two layers. As noted elsewhere, herein, in some cases, the opposing nanowire populations may be further processed to permit such electrical communication, including, e.g., thermal annealing, or the like. The use of a dual semiconductor system, e.g., as shown in FIG. 6B, may obviate the need for any organic species within the active layer, e.g., conductive polymers, or the like, and is expected to improve charge separation efficiencies by speeding conduction of their respective carriers to their respective electrodes, and thus prevent recombination of the charges within the active layer.

In one embodiment, an electrical device of the invention includes a porous substrate having a plurality of apertures disposed therethrough, the porous substrate having an overall surface area that includes an interior wall surface area of the plurality of apertures, and a plurality of conductive or semiconductive nanowires attached to and electrically coupled to the porous substrate. An exemplary photovoltaic device includes a first such electrical device, wherein the plurality of nanowires comprises a first energy band gap, and a second such electrical device, wherein the plurality of nanowires comprises a second energy band gap. The first and second energy band gaps display a type-II band gap offset relative to each other, and the nanowires of the first electrical device are in electrical communication with the nanowires of the second electrical device, so as to allow charge separation between the first and second electrical devices upon exposure to light.

As will be readily appreciated, the photovoltaic devices described above are primarily for the illustration of the applicability of the substrates of the invention to certain electronic or optoelectronic applications. Those of skill in the art will recognize a broad range of other electronic devices in which such substrates would be useful.

In still another exemplary application, porous nanofiber or nanowire coated substrates are encased in matrix components, e.g., a polymer matrix, for use as a composite matrix, including the underlying mesh. Such applications are particularly useful where the nanofibers are being employed as a bulk material to enhance the functionality of the composite matrix. Such enhancements include electrical enhancements, e.g., where the composite is being used as a dielectric material, or to partially orient the nanofibers in optoelectric applications, e.g., photovoltaics, structural enhancements where the presence of the nanofibers imparts unique structural characteristics to the matrix, e.g., tensile strength, elasticity etc.

Figure 7:
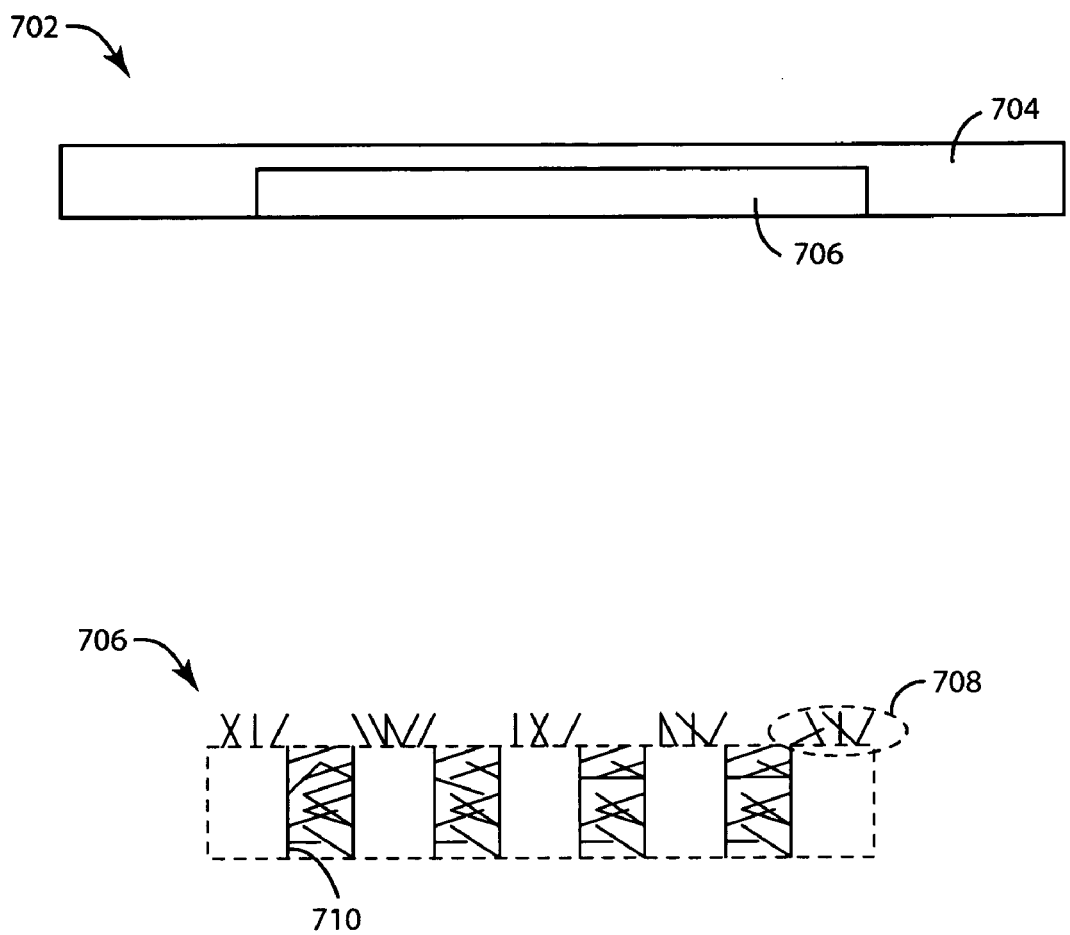
FIG. 7 is a schematic illustration of an article of the invention used as a lattice for incorporation into a composite matrix for use as, e.g., a dielectric layer.

FIG. 7 schematically illustrates a composite matrix incorporating the materials of the invention. As shown, a film of composite material 702 includes within a matrix material, e.g., a polymer, ceramic, glass or the like, a porous substrate 706 that includes nanofibers 708 disposed upon its surface 710, including within pores or apertures 710. The porous substrate is generally immersed or impregnated with matrix material 704 to provide film 702. As noted above, these composite films are then applied in a variety of applications, e.g., as conductive films, dielectric films, etc.

Figure 8A:
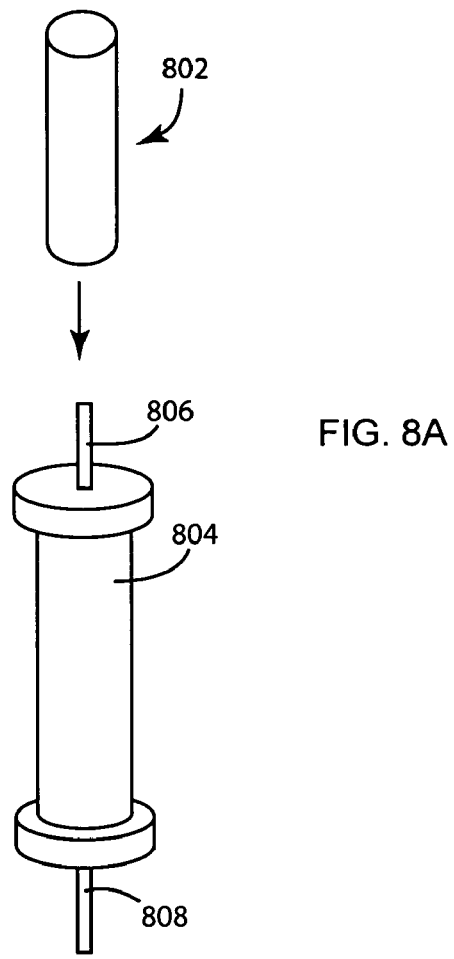
FIG. 8 Panels A and B schematically illustrate separation media incorporating the substrates of the invention in conjunction with column apparatus for performing chromatographic separations.
Figure 8B:
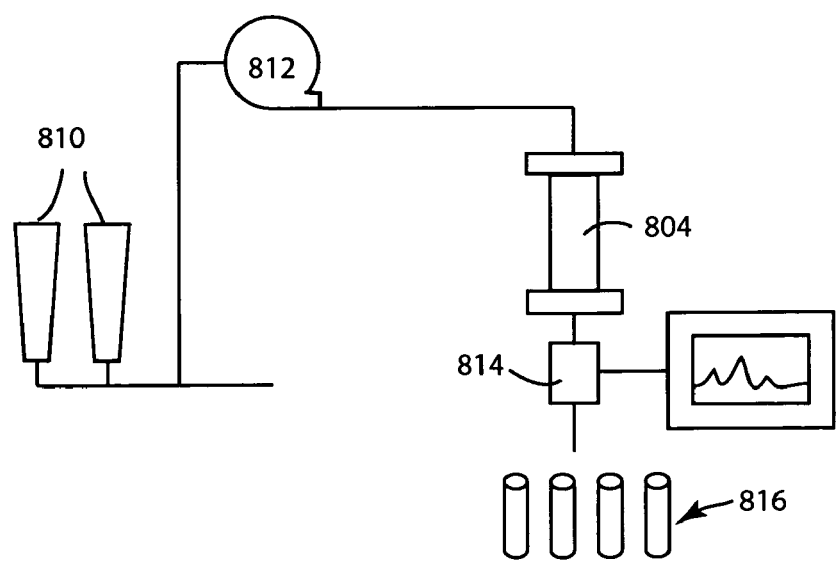

FIGS. 8A and 8B schematically illustrate the use of porous substrates to provide high surface area matrices for separation applications, e.g., chromatography. In particular, as shown in FIG. 8A, a porous substrate 802 that has nanofibers attached to its surface is provided. As noted, this porous substrate may be provided in a number of different forms. For example, substrate 802 may comprise a mesh or screen that is rolled into a cylinder, either before or after the fibers are attached or grown upon it. Alternatively, the substrate may comprise a solid, but sintered or fritted material, e.g., metal or glass. In still other aspects, the substrate may comprise a fibrous material, e.g., glass wool, woven fabric etc., that is shaped into the desired shape, e.g., a cylinder 802 as shown, either by forming the material as such or packing the material into a cylindrical (or other shaped) housing. Again, such shaping may take place either before or after the nanofibers have been grown or otherwise attached to the surface of the porous material.

The substrate 802 is then placed into a column 804, which includes an inlet 806 and an outlet 808 through which fluids are flowed into and out of the column during a separation operation. As shown in FIG. 8B the column 804 is then connected to appropriate liquid handling equipment, e.g., gradient makers 810, pumps 812, detectors 814, fraction collectors 816, and the like, for carrying out chromatographic separations.

As will be apparent, the separation matrices incorporating the substrate materials of the invention may encompass any of a variety of the different substrate structures and conformations, employ any number of a variety of different types of nanofibers, as described elsewhere herein. Such structures, conformations and compositions are generally selected depending upon the particular application to which they are to be put and which will generally be appreciated by those of ordinary skill in the art.

E. Reinforcing Lattice for Composite Materials

In still another aspect of the invention, the porous, nanofiber bearing substrates of the invention form the lattice of a composite material to enhance the integration of the lattice and improve the structural characteristics of the overall composite material. In particular, a number of composite materials include a lattice that provides the underlying structural integrity that supports an additional material, e.g., epoxies or other polymers, ceramics, glasses, etc. For example, composites of fiberglass cloth encased in epoxy resins, or other polymers are routinely used in a variety of different applications, including, e.g., furniture, surfboards and other sporting goods, auto body repairs, and the like. Likewise, carbon fiber cloths or substrates are also generally encased in a polymer or epoxy resin before they are formed into the desired shape. Ultimately, these composite materials generally possess structural characteristics, e.g., strength to weight ratios, that are better than most other materials. Without being bound to a particular theory of operation, it is believed that the interaction of the encasing material and the lattice material is of significant importance in these structural characteristics. Specifically, it is believed that by enhancing the interaction of the two components of the composite, e.g., improving integration of one into the other, will improve the strength of the ultimate composite material. Because the nanofiber bearing porous substrates of the invention benefit from extremely high surface areas, as compared to that of the porous substrate alone, it is expected that they will possess substantially greater interactivity with the surrounding encasing material, e.g., the epoxy. As such, another aspect of the invention includes the use of the porous substrates having nanofibers deposited thereon, as a lattice material for a composite material.

Figure 11:
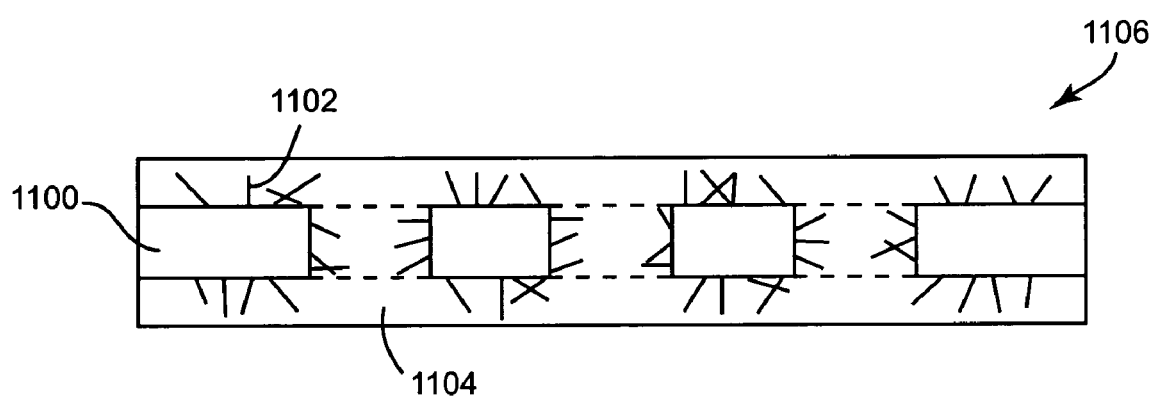
FIG. 11 illustrates a composite material that employs the porous substrates of the invention disposed within a matrix material.

A general illustration of this aspect of the invention is shown in FIG. 11. As shown, a porous substrate 1100 having a surface that includes nanofibers 1102, is immersed within a matrix material, e.g., hardened polymer 1104 to provide a composite material 1106, that may be fabricated into a variety of different materials or articles of manufacture.

As noted, a variety of fabrics are generally incorporated into composite matrices as a supporting lattice for the ultimate material. For example, carbon fiber composites typically employ a woven carbon fiber material which is then intercalated with a resin, e.g., an epoxy or other polymeric material. The composite material is then formed into a desired shape and allowed to cure. Alternatively, the desired shape may be formed post curing, e.g., by sanding or otherwise sculpting the hardened material. Similarly, woven glass fabrics are used in fiberglass composite materials by intercalating the fabric with an appropriate matrix, e.g., an epoxy, etc.

In the context of the present invention, a porous substrate that has nanofibers deposited upon it or attached to its surface (s) is used as the lattice material for the resultant composite. The nanofiber material is intercalated with a matrix material that substantially or at least partially fills the voids within the material. Because of the extremely high surface area, the matrix binds to and integrates the lattice material extremely well, resulting in a stronger composite material than those based simply on a porous substrate alone, e.g., in the absence of the nanofiber surfaces. Such composite materials may be generally employed in a number of applications where high strength to weight ratios are desired, such as in lightweight engineered parts, e.g., bicycles, tennis rackets, automotive parts, aviation parts, satellite and other extraterrestrial equipment and parts, etc.

While virtually any porous substrate material, e.g., as described elsewhere herein, may be employed as the supporting lattice, for a number of applications, a flexible lattice material is more desirable, as it may be later conformed to a desired shape, e.g., molded or sculpted, for a particular application. In at least a first preferred aspect, flexible mesh materials are used as the supporting lattice. Such materials include porous polymeric sheets, porous metal sheets, flexible porous glass sheets, e.g., sintered glass sheets, and the like. In other preferred aspects, porous woven cloth-like materials are employed as the lattice, including, e.g., woven polymeric fabrics, (e.g., polyesters, nylons, polyetherketones, polyaramid, etc.), woven glass fabrics (e.g., fiberglass fabrics, glass wool, etc), carbon or graphite fiber fabrics, Kevlar fabrics, and metallic fiber fabrics (e.g., titanium, stainless steel, nickel, platinum, gold, etc.). The wide range of different porous, flexible substrates for use as the lattice material will generally be appreciated by those of ordinary skill in the art, and may generally be varied to accomplish the needs of the ultimate application, e.g., light weight and/or enhanced strength, materials compatibility, and the like.

Like the lattice material, the type of material used as the intercalating matrix for the lattice will generally depend upon the nature of the application to which the material is to be put. By way of example, inorganic materials may be employed as the matrix, including glass, ceramics or the like. Alternatively, and preferably, polymeric matrices are employed, including thermosets, such as polyester, epoxy, urethane and acrylate resins, and the like, thermoplastics and/or thermoplastic elastomers, such as polyethylene, polypropylene, nylon, PFA, and the like. Typically any of these matrix materials may be deposited as a polymer over the lattice substrate and allowed to intercalate throughout the nanofiber mesh. Subsequently, the matrix material is allowed to or caused to cure in situ. Alternatively, polymeric matrices may be intercalated as a monomeric solution and polymerized in situ to "cure" the matrix in place. In still further alternate aspects, the polymeric matrix may be deposited over the porous substrate bearing the nanofibers, using a vapor phase or solvent deposition process, e.g., as described above for the cross-linking of nanofibrous mats. The full range of different polymers and their utility in a wide range of different applications will be readily apparent to those of ordinary skill in the art.

F. Protected Nanofiber Surfaces

A variety of applications exist for articles with nanofiber-enhanced surfaces, as noted above; for example, implantable medical devices such as stents, nanofiber-enhanced fabrics, nanofiber arrays, membranes, and the like. However, such nanofiber-based devices frequently present a relatively fragile nanofiber surface at which even light contact with other objects (e.g., packaging material, skin, etc.) can cause nanofiber breakage, matting, and removal. Techniques for strengthening and/or protecting nanofiber surfaces are thus desirable.

As described above, nanofibrous mats can be fused, coated, or crosslinked at points of nanofiber contact. Similar techniques can be used to protect essentially any population of nanofibers, whether grown in situ or deposited on a substrate, that would benefit from protection from abrasion, breakage, etc.

In one aspect, the invention provides methods of stabilizing nanofibers (e.g., nanowires). In the methods, a population of nanofibers is provided, and a coating is formed on the nanofibers. The coating is contiguous between adjacent nanofibers in the population.

In one class of embodiments, a first material comprising the nanofibers is different from a second material comprising the coating. The first and second materials are optionally unrelated or related. Thus, in certain embodiments, the second material is an oxide of the first material. For example, the nanofibers can comprise silicon and the coating silicon oxide, the nanofibers can comprise titanium and the coating titanium oxide, etc. Generally, regardless of the composition of the nanofibers, the coating optionally comprises an oxide, e.g., an oxide of silicon, titanium, aluminum, magnesium, iron, tungsten, tantalum, iridium, or ruthenium. For example, titanium nanowires can be oxidized to form the titanium oxide coating, or other nanowires can be coated with titanium which is then oxidized to form the coating. The nanofibers are optionally sintered or oxidized in situ during synthesis, or after synthesis and/or deposition by a rapid thermal oxidation (RTO) technique, e.g., in embodiments in which any substrate to which the nanofibers are attached is compatible with the high temperatures required for RTO. As another example, as described above, silicon nanowires (nanofibers) can be synthesized (e.g., at about 480° C.) and then coated with polysilicon (e.g., at about 600° C.) to thicken and strengthen the nanowires and to fuse wires together at wire-wire junctions.

It will be evident that the coating is not limited to comprising an oxide or polysilicon, but can include essentially any material that imparts a desirable property to the resulting coated nanofiber population, e.g., stability or a desirable electrochemical or dielectric property. Additional exemplary coatings include polymers, carbon, carbides, and nitrides. For example, silicon nanowires can be synthesized and then coated with carbon and silicon carbide (resulting, e.g., from conversion of some of the silicon nanowire) or with TaN (e.g., by atomic layer deposition).

In one aspect, the population of nanofibers is provided by synthesizing the nanofibers on a surface of a substrate. Exemplary substrates have been described herein, e.g., porous, curved, woven, and/or flexible substrates, but it will be evident that the methods are not limited to nanofibers synthesized on or attached to such substrates. The nanofibers can be preformed and deposited on a substrate. The substrate is optionally non-porous. The substrate optionally comprises or covers at least a portion of a surface of an implantable medical device.

The coated population of nanofibers preferably retains any desirable surface properties of the original nanofiber population, for example, minimal contact area with objects, a highly porous three-dimensional structure, superhydrophobicity, low biological growth and attachment, or the like. Relatedly, the coating can provide desirable surface characteristics; for example, the coating can comprise a material that is readily functionalized (e.g., silicon oxide). In one class of embodiments, the methods include functionalizing the coating with a chemical binding moiety, a hydrophobic chemical moiety, a hydrophilic chemical moiety, a drug (e.g., to inhibit cell or bacterial growth), or the like.

Populations of nanofibers (e.g., nanowires) formed by the methods are another feature of the invention. One general class of embodiments provides a population of nanofibers that includes nanofibers and a coating on the nanofibers, wherein the coating is contiguous between adjacent nanofibers in the population. A device bearing such a population, e.g., an implantable medical device, is likewise a feature of the invention.

In a related aspect, a nanofiber surface is protected by a layer of porous (or alternatively, non-porous) material. A nanofiber bearing substrate can have a first layer of porous material disposed on its surface. For example, a nanowire coated fabric, flexible mesh, or other flexible and/or porous substrate can be protected with a porous material layer that can, e.g., be heat sealed or ultrasonically welded to the substrate, on one or both sides of the substrate. This protects the delicate nanofiber bearing substrate from abrasion or similar damage, while still allowing vapors and/or liquids to penetrate to the substrate. Exemplary porous materials include, but are not limited to, non-woven polypropylene porous material (for example, similar to that used in Celgard™ laminates, Hoechst Celanese). Additional weldable materials include polyethylene, polystyrene, acetate, and thin pretreated Teflon™ layers. The protective layer(s) are optionally flexible or inflexible.

The substrate is optionally sandwiched between two layers of porous or non-porous material; for example, between two layers of porous material, or between a porous layer on one side and a non-porous layer on the other side. It will be evident that choice of material(s) for the protective layer(s) can depend on the desired application. For example, a flexible fabric substrate can be sandwiched between flexible porous layers for certain applications, or between a porous layer and an inflexible non-porous layer for other applications. As noted, a protective layer can be heat sealed or welded to the substrate. Similarly, the protective layer can be attached to the substrate by sewing or use of an adhesive.

Figure 14:
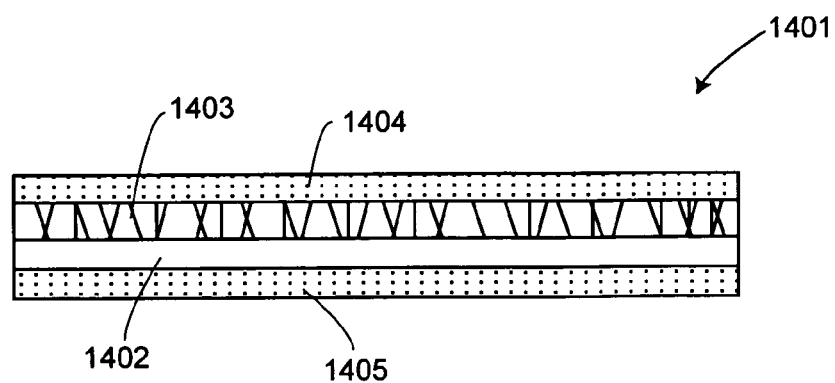
FIG. 14 schematically illustrates protection of a nanofiber-bearing substrate by disposing it between layers of porous material.

FIG. 14 schematically illustrates protection of a nanofiber bearing substrate by a porous layer. As shown in FIG. 14, substrate 1402 bearing nanofibers 1403 is provided. The substrate is typically a flexible porous substrate, but need not be; in certain embodiments, it is a rigid and/or non-porous substrate. First layer 1404 of porous material is disposed on the first surface of the substrate and second layer 1405 of porous material is disposed on the second surface of the substrate, providing article 1401. Nanofibers 1403 are protected from abrasion, matting, removal, breakage, etc. by being sandwiched between the porous material layers.

G. Nanofiber Synthesis

In one aspect, the porous substrates of the invention are useful as lattices for synthesis of large quantities and/or high densities of long, unbranched nanofibers, particularly nanowires. Silicon nanowires, for example, are desirable materials for inter alia a variety of macroelectronic applications. Such nanowires are typically required to be long (e.g., at least about 40, 50, or 60 µm in length), straight, and branch free. However, large quantities of such long and unbranched nanowires are not readily obtained through current synthesis techniques.

Currently, nanowires are typically grown on flat wafer substrates. When non-oriented wire growth methods (e.g., $SiH_4$), which are simpler and less expensive to implement than oriented growth methods, are used to produce nanowires, collisions between growing wires lead to growth termination, branched wire formation, and the like. Collisions between nanowires can be limited by reducing nanowire density (e.g., by reducing gold colloid particle density) and/or length; however, these tactics obviously do not result in inexpensive, simple production of large quantities of nanowires and/or long nanowires. For example, for non-oriented growth on a flat substrate, to obtain 40 µm long nanowires with only 10% collisions per wire, gold colloid particle density can be at most 0.01 particle/$µm^2$, based on both theoretical predictions and experimental results. Yield of long, straight, unbranched nanowires from even non-oriented growth techniques can be improved by growing the nanowires on high surface area porous substrates or curved substrates.

In other embodiments, nanofibers are grown on porous surfaces to provide the semipermeable membranes and other articles noted above, for example, and need not be long, straight, and/or unbranched.

Accordingly, one general class of embodiments provides methods of producing nanofibers. In the methods, a substrate comprising a) a plurality of apertures disposed therethrough, the substrate comprising an overall surface area that includes an interior wall surface area of the plurality of apertures, or b) a curved surface is provided. A plurality of nanofibers is synthesized on the substrate, wherein the resulting nanofibers are attached to at least a portion of the overall surface area of the substrate of a) or to at least a portion of the curved surface of b). The curved surface is preferably convex when used for growth of long unbranched nanofibers, but can alternatively or additionally be concave. The curved surface optionally has a nonzero mean radius of curvature over a significant fraction of the substrate's surface (e.g., a cylindrical fiber-shaped substrate) or over its entire surface (e.g., a microsphere or similar substrate). It will be evident that many substrates can be described as either or both porous and/or curved; for example, a fibrous mat can be described as a whole as a porous substrate or on the level of individual constituent fibers as a curved substrate.

Figure 15A:
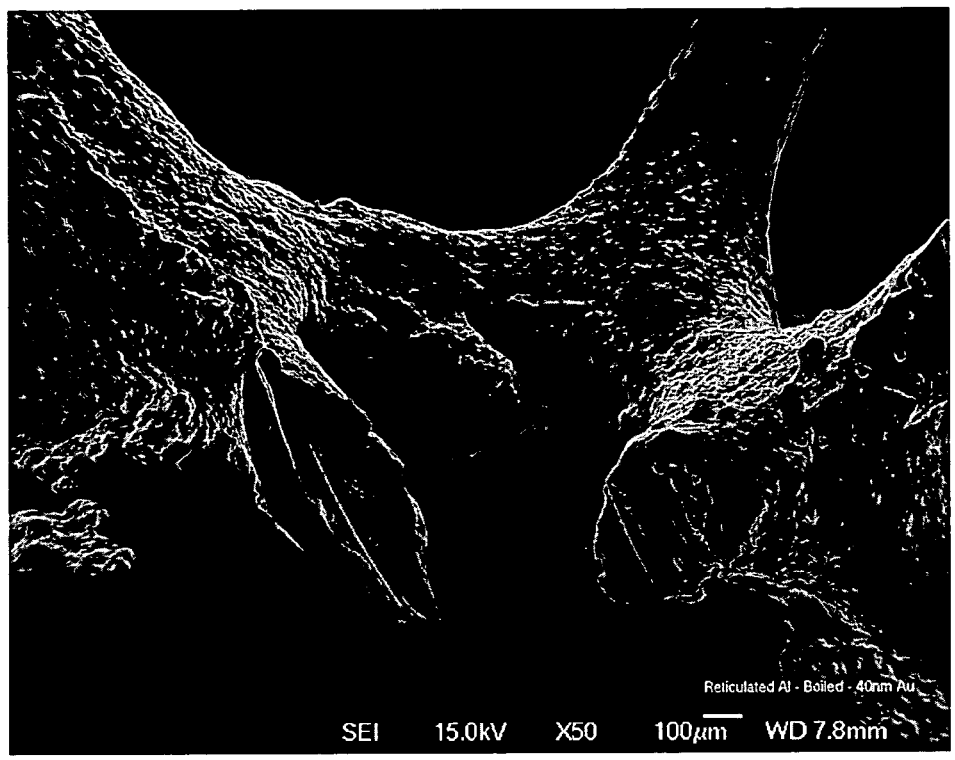
FIG. 15 Panel A depicts an electron micrograph of reticulated aluminum. Panel B depicts an electron micrograph of nanowires grown on a reticulated aluminum substrate.
Figure 15B:
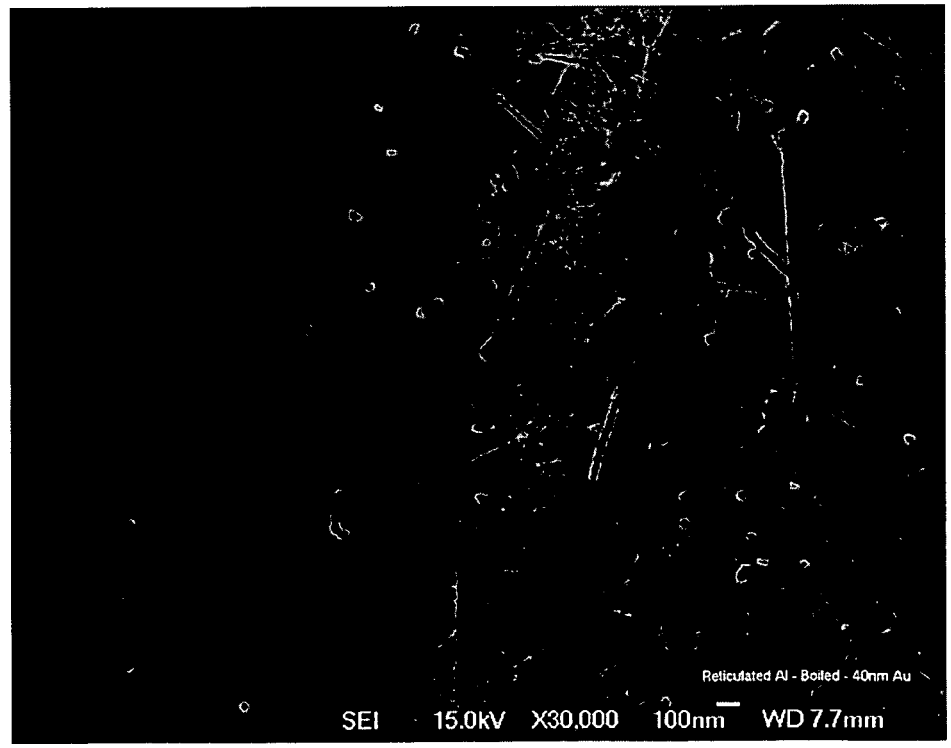
Figure 16B:
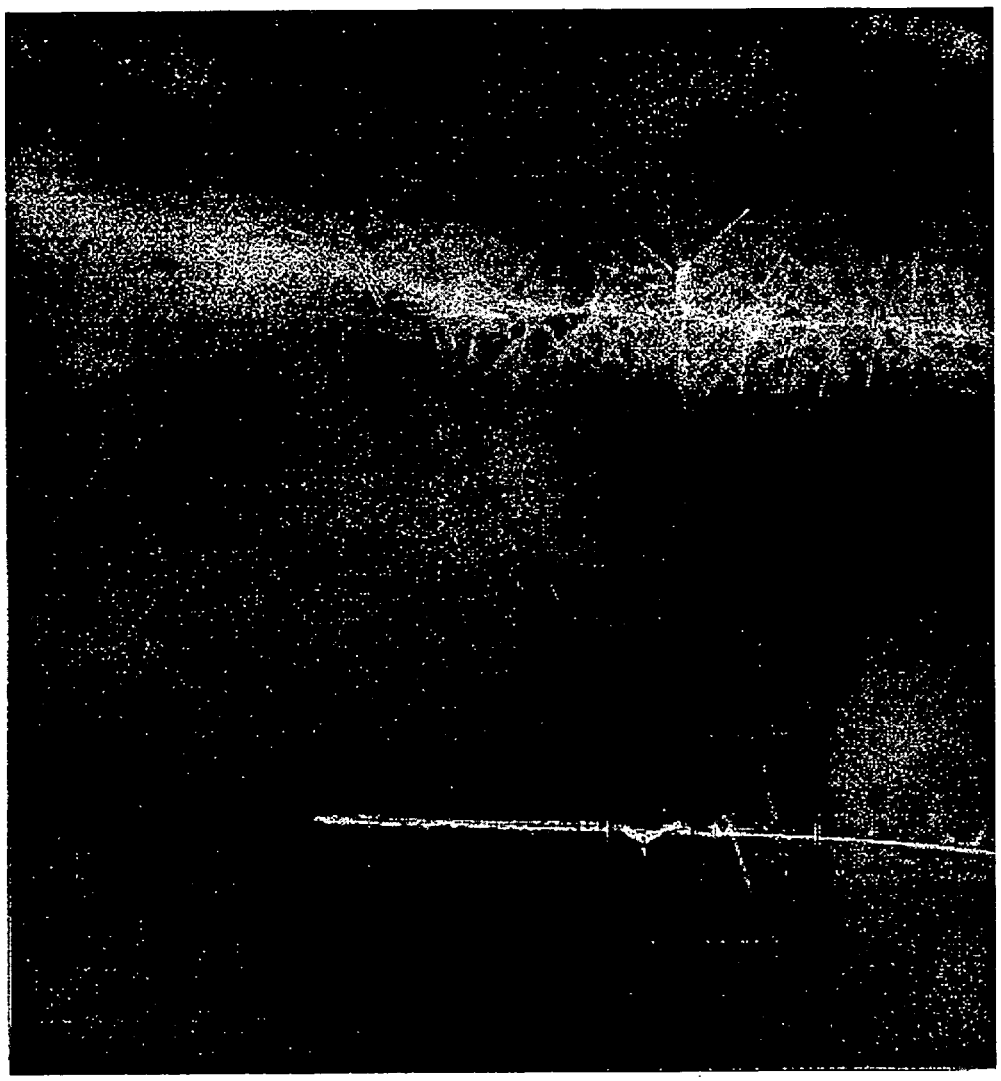
FIG. 16 depicts silicon nanowires grown on quartz fiber filters (Panels A-B), grown on quartz fiber filters and removed from the substrate by sonication (Panels C-D), and grown on a glass fiber (Panel E).
Figure 16D:
Figure 16C:
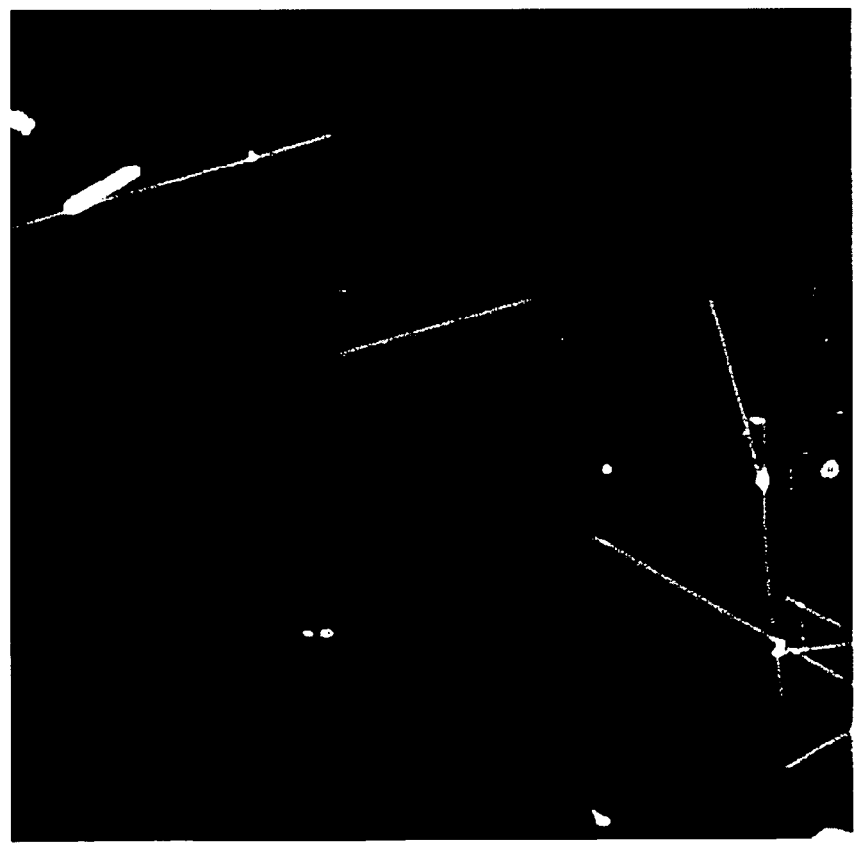
Figure 16E:
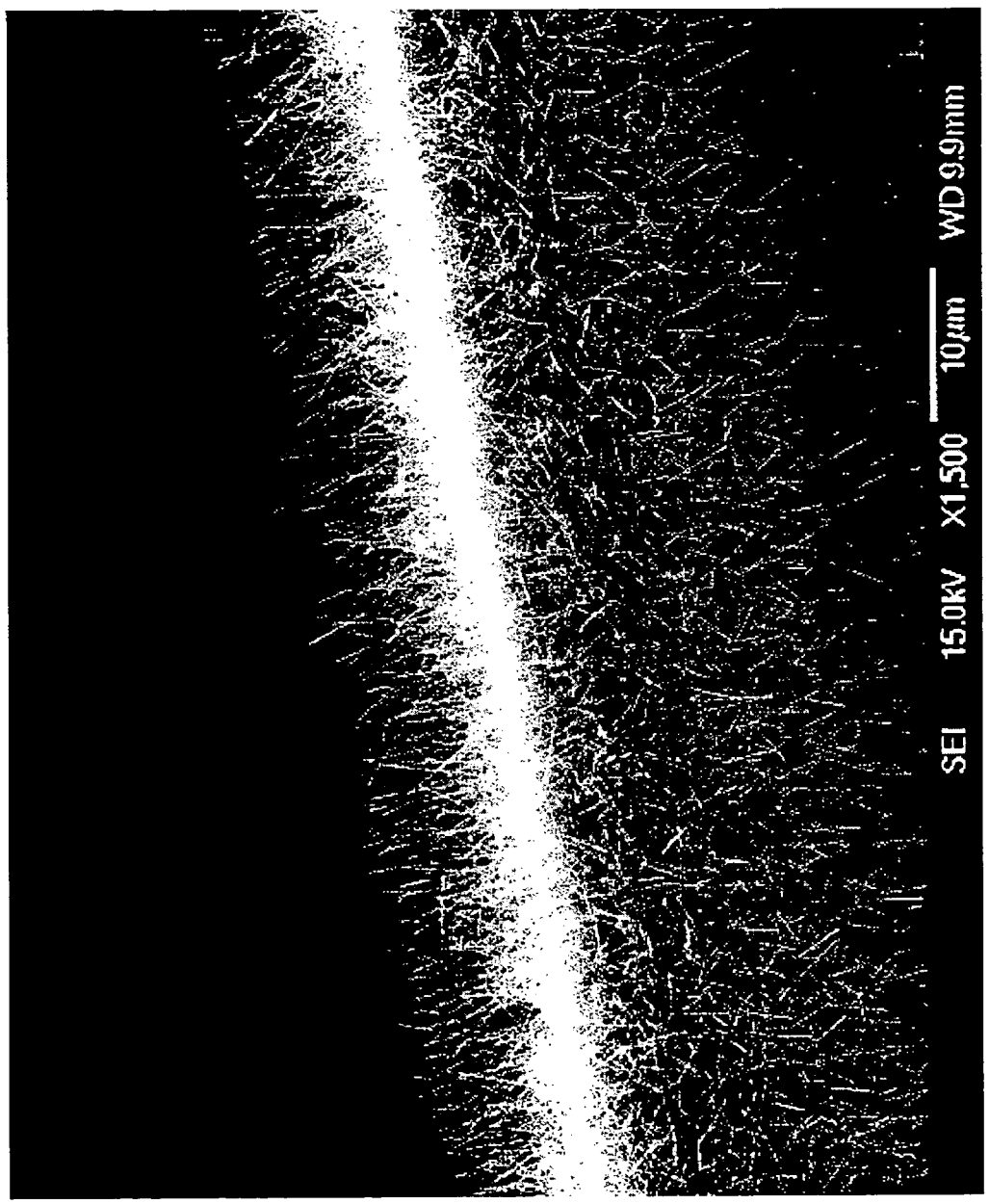

A number of exemplary substrates have been described above. For example, the substrate can comprise a solid substrate with a plurality of pores disposed through it, a mesh, a woven fabric, or a fibrous mat. As other examples, the substrate can comprise a plurality of microspheres or other microparticles (e.g., glass or quartz microspheres), a plurality of glass or quartz fibers (e.g., microfibers, fiberglass, glass or quartz fiber filters), or a foam (e.g., a polymer or metal foam such as reticulated aluminum). FIG. 15A shows reticulated aluminum, while FIG. 15B illustrates nanowires grown on a reticulated aluminum substrate. Essentially any other porous or curved substrate can also be employed in the methods; preferred substrates are chemically compatible with any chemicals used to synthesize the nanofibers (e.g., have low levels of magnesium), can withstand the synthesis temperatures, can have catalyst dispersed on them (if required), and facilitate clean harvest of nanofibers from the substrate (if desired). In certain embodiments, e.g., for various filtration applications noted above, the porous substrate preferably has an effective pore size of less than 10 µm, less than 1 µm, less than 0.5 µm, or even less than 0.2 µm. In other embodiments, e.g., for synthesis of long nanowires, the porous substrate preferably has an effective pore size of at least 25 µm, at least 50 µm, at least 100 µm, or more, depending on the desired nanowire length (for example, the width of the apertures in a mesh used for nanowire synthesis would be at least about twice the desired length of the nanowires).

The nanofibers can comprise essentially any type of nanofibers, e.g., silicon nanowires, carbon nanotubes, or any of the other nanofibers noted above. In certain embodiments, the nanofibers comprise nanowires, and the methods include synthesizing the plurality of nanowires by depositing a gold colloid on at least a portion of the overall surface area of the substrate of a) or on at least a portion of the curved surface of b) and growing the nanowires from the gold colloid with a VLS synthesis technique.

The methods optionally include surrounding or at least partially encapsulating the substrate and the resulting attached nanofibers with a matrix material; dissolving a soluble substrate following synthesis of the nanofibers on the substrate; forming a coating on the resulting nanofibers, wherein the coating is contiguous between adjacent nanofibers; disposing a layer of porous material on the resulting nanofibers (and optionally disposing the substrate on a second layer of porous material, sandwiching the nanofiber-bearing substrate); and/or functionalizing the nanofibers (e.g., by attaching a chemical moiety or nanocrystal), as described above.

FIG. 16 shows electron and optical micrographs that illustrate certain aspects of the invention. FIG. 16E shows a single glass fiber covered by silicon nanowires. The glass fiber substrate was chemically treated by soaking in a polylysine solution for 20 minutes to attract gold colloid to its surface. Silicon nanowires were grown from the gold colloid on the substrate using a chemical vapor deposition (CVD) method; a silane reaction at a moderately low temperature (480° C., much lower than the high temperatures of approximately 900° C. or more used by the industry to grow bulk single crystalline silicon) resulted in single crystalline silicon nanowires. Quartz fiber filters have also been used as substrates for growth of silicon nanowires. Two quartz fiber filters (AQFA04700 from Millipore and QF-200 from F&J Specialty Products) were used to grow silicon nanowires. As described for growth on glass fiber substrates, nanowires were grown on the quartz fiber filters at 480° C. for 90 minutes (FIGS. 16 A-B). The silicon nanowires were removed from the filters by sonication (see, e.g., FIGS. 16 C-D, which depict the resulting detached nanowires).

Growth of nanowires on porous or curved substrates such as meshes, microfibers, microbeads, or microporous glass or quartz materials offers a number of advantages over growth on planar substrates. For example, compared to a flat wafer surface, microfibers, microbeads, or microporous surfaces can grow nanowires with fewer collisions per wire at the same wire length and catalyst particle density due to the surface curvature of the substrate. Therefore, it is possible to obtain straight longer wires free of branches at higher yield on curved or porous substrates than on flat surfaces. The total surface area of the micro substrate can be easily controlled, for example, by varying the diameter and the volume of the micro-materials (e.g., the thickness and pore size for fiber membranes, or the diameter of beads). The high yield of nanowires from the micro substrates can significantly reduce the cost of making nanowires. Straight branch-free silicon nanowires can be produced using a silane method or other un-oriented nanowire growth method on micro substrates. If desired, the resulting nanowires can be easily removed by sonication after synthesis, due to the flexibility and/or small size of the substrate materials. In addition, when a porous substrate is employed, reacting gases can readily reach substantially all of the catalyst particles deposited on the substrate.

Figure 17A:
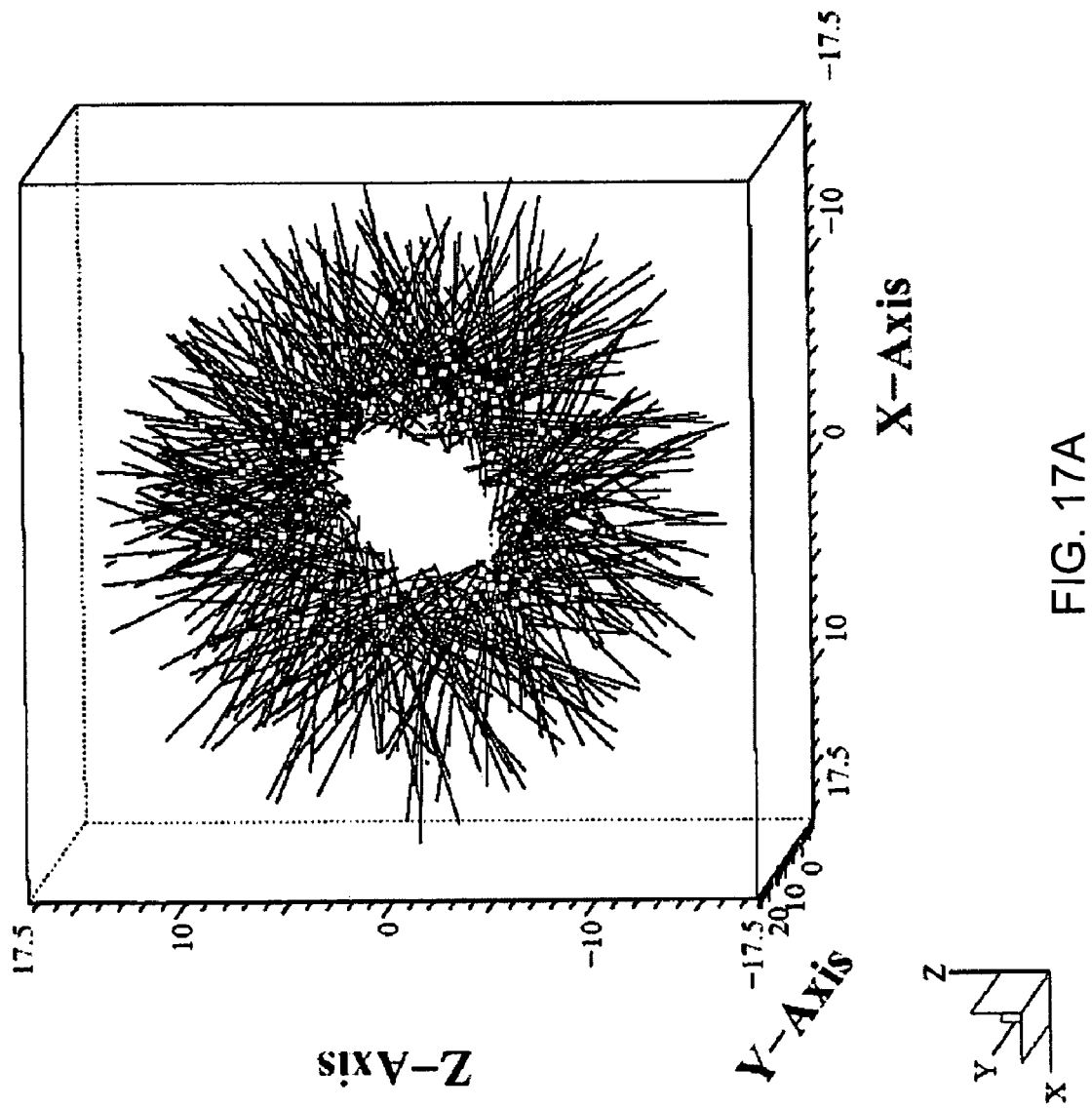
FIG. 17 Panel A depicts simulated nanowires growing on a 5 μm diameter fiber. Panel B depicts a graph of the collisions per nanowire as a function of fiber radius for simulated nanowire growth on a fiber.
Figure 17B:
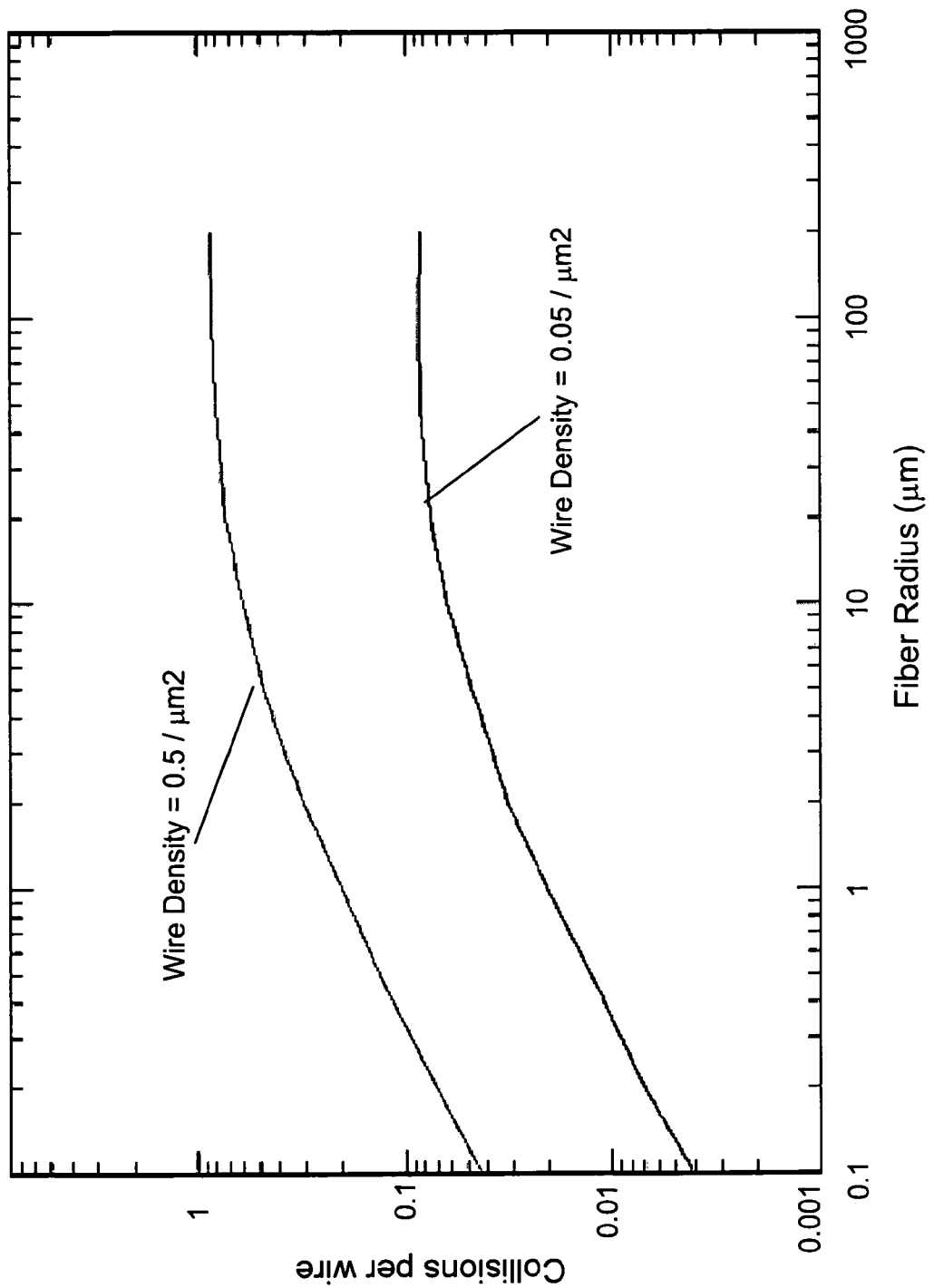

Simulations of nanowire growth provide an additional illustration of the advantages offered by curved substrates as lattices for nanowire growth. FIG. 17A shows simulated randomly oriented 10 μm long nanowires growing on a 5 μm diameter fiber at a density of 0.5 nanowires/μm$^2$. Light squares mark collisions between wires. FIG. 17B graphs the number of collisions per nanowire as a function of the radius of the fiber, at two different nanowire densities: 0.05 nanowires/μm$^2$ and 0.5 nanowires/μm$^2$. As the radius of the fiber increases (and therefore, the curvature of the fiber's surface decreases), the number of collisions per wire approaches that observed on a flat surface. As is evident from the graph, the number of collisions per wire is affected by wire density and also by the diameter of the fiber. A higher density of high-quality nanowires (long and unbranched nanowires having few collisions per wire) can be obtained on a curved surface than a flat one. Furthermore, at a constant density of nanowires (wires/area), the number of collisions per wire decreases with decreasing fiber radius.

Accordingly, the yield of long and/or unbranched nanofibers produced by the methods is optionally greater than the yield of comparable nanofibers produced by synthesis on flat substrates. In one class of embodiments, yield of the resulting nanofibers having a length greater than 10 μm (e.g., greater than 20 μm, 30 μm, 40 μm, 50 μm, or 60 μm) is at least 10% greater than yield of nanofibers of that length synthesized on a planar non-porous substrate (i.e., a solid planar substrate with no apertures or pores therethrough) of the same surface area, using substantially the same growth process. The yield from the methods is optionally at least 25%, 50%, 75%, or even 100% greater than the yield from growth on the planar non-porous substrate. For example, growth of nanowires using a non-oriented synthesis technique, e.g., VLS growth from a gold colloid, can produce more long nanofibers on the substrate of a) or b) than on a flat non-porous substrate of comparable surface area using substantially the same growth process (e.g., the same temperature, colloid deposition density, growth times, process gases, and the like).

In one class of embodiments, the curved substrate of b) has at least one dimension (typically, a cross-sectional diameter) that is less than 1000, less than 500, less than 100, or less than 50 times an average cross-sectional diameter of the nanofibers. The at least one dimension of the substrate is optionally greater than 2, greater than 5, greater than 10, or greater than 20 times the average cross-sectional diameter of the nanofibers. The substrate optionally comprises a different material than the nanofibers.

As in the example above, the nanofibers are optionally removed from the surface area of the substrate of a) or the curved surface of b) following synthesis of the nanofibers, e.g., by sonicating the substrate, to produce a population of detached nanofibers. As noted, the method can produce long nanowires. Thus, in one class of embodiments, at least 10% (e.g., at least 20%, 30%, 40%, 50%, 60%, 70%, 80%, or even 90%) of the nanofibers in the population of detached nanofibers have a length greater than 10 μm, 20 μm, 30 μm, 40 μm, 50 μm, or 60 μm, while at most 50% (e.g., at most 40%, 30%, 20%, or 10%) of the nanofibers have a length less than 10 μm. Optionally, at least 50%, 60%, 70%, 80%, or 90% of the nanofibers in the population of detached nanofibers are unbranched, while at most 50%, 40%, 30%, 20%, or 10% of the nanofibers are branched. The nanofibers can have similar length and branched/unbranched distributions when attached to the substrate.

The methods optionally include characterizing the nanofibers, attached to the substrate and/or after their removal from the substrate, by determining one or more of: their length, diameter, percent branched/unbranched, collision with other nanowires per nanowire or per unit length of the nanowires, and the like, per nanowire or as an average or distribution.

Articles or populations of nanofibers produced by the methods form another feature of the invention. Thus, one exemplary class of embodiments provides an article comprising a substrate having a curved surface, and a plurality of nanofibers (e.g., nanowires) attached to at least a portion of the curved surface of the substrate. The substrate can comprise, e.g., a plurality of microspheres or one or more glass fiber, quartz fiber, metallic fiber, or polymer fiber. An implantable medical device comprising an article of the invention, e.g., attached to and covering at least a portion of the surface of the implantable medical device, is also a feature of the invention.

All publications, patents, patent applications, and/or other documents cited in this application are incorporated by reference in their entirety for all purposes to the same extent as if each individual publication, patent, patent application, and/or other document were individually indicated to be incorporated by reference for all purposes. Although the present invention has been described in some detail by way of illustration and example for purposes of clarity and understanding, it will be apparent that certain changes and modifications may be practiced within the scope of the appended claims.

What is claimed is:

1. A method of producing a vapor absorbing fabric, the method comprising:

providing a porous activated carbon fabric substrate that comprises a plurality of apertures disposed therethrough, the substrate comprising an overall surface area that includes an interior wall surface area of the plurality of apertures; and providing a plurality of nanocrystals attached to at least a portion of the overall surface area of the activated carbon fabric substrate, which nanocrystals absorb or decompose at least one non-organic gas, wherein the nanocrystals comprise ZnO, CuO, Cu$_2$O, Al$_2$O$_3$, TiO$_2$, MgO, FeO, Fe$_2$O$_3$, MnO$_2$, Mn$_x$O$_y$, or Zn, thereby producing the vapor absorbing fabric.

* * * * *

UNITED STATES PATENT AND TRADEMARK OFFICE
CERTIFICATE OF CORRECTION

PATENT NO. : 7,553,371 B2  
APPLICATION NO. : 11/331445  
DATED : June 30, 2009  
INVENTOR(S) : Robert Dubrow et al.

Page 1 of 1

It is certified that error appears in the above-identified patent and that said Letters Patent is hereby corrected as shown below:

On the title page (75):  
Please amend the list of inventors to read as follows:

Inventors: Robert Dubrow, San Carlos, CA (US); Carlos Guillermo Casillas, Santa Cruz, CA (US); William P. Freeman, San Mateo, CA (US); Chunming Niu, Palo Alto, CA (US)

Signed and Sealed this

Eighteenth Day of August, 2009

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,553,371 B2 | Page 1 of 1 |
| APPLICATION NO. | : 11/331445 | |
| DATED | : June 30, 2009 | |
| INVENTOR(S) | : Dubrow et al. | |

It is certified that error appears in the above-identified patent and that said Letters Patent is hereby corrected as shown below:

In column 1, please delete the paragraph beginning on line 23 and ending on line 27 and insert the following:

--This invention was made with Government support under W911QY-05-C-0081 awarded by the US Army Soldier Systems Center. The Government has certain rights in the invention.--

Signed and Sealed this
Twenty-second Day of November, 2011

David J. Kappos
*Director of the United States Patent and Trademark Office*